(12) United States Patent
Zhao et al.

(10) Patent No.: US 10,584,104 B2
(45) Date of Patent: Mar. 10, 2020

(54) CARBOXYLIC ACID URAT1 INHIBITOR CONTAINING DIARYLMETHANE STRUCTURE, PREPARATION METHOD AND USE THEREOF

(71) Applicant: TIANJIN INSTITUTE OF PHARMACEUTICAL RESEARCH CO., LTD., Tianjin (CN)

(72) Inventors: Guilong Zhao, Tianjin (CN); Wei Liu, Tianjin (CN); Qian Shang, Tianjin (CN); Zhixing Zhou, Tianjin (CN); Yuli Wang, Tianjin (CN); Yuquan Li, Tianjin (CN); Haizhi Zhang, Tianjin (CN); Chuan Li, Tianjin (CN); Changying Liu, Tianjin (CN); Yuqiang Liu, Tianjin (CN); Yafei Xie, Tianjin (CN); Jingwei Wu, Tianjin (CN); Huihui Chen, Tianjin (CN); Weiren Xu, Tianjin (CN); Lida Tang, Tianjin (CN)

(73) Assignee: TIANJIN INSTITUTE OF PHARMACEUTICAL RESEARCH CO., LTD., Tianjin (CN)

(*) Notice: Subject to any disclaimer, the term of this patent is extended or adjusted under 35 U.S.C. 154(b) by 54 days.

(21) Appl. No.: 15/570,151

(22) PCT Filed: Apr. 28, 2016

(86) PCT No.: PCT/CN2016/080468
§ 371 (c)(1),
(2) Date: Oct. 27, 2017

(87) PCT Pub. No.: WO2016/173503
PCT Pub. Date: Nov. 3, 2016

(65) Prior Publication Data
US 2018/0134670 A1 May 17, 2018

(30) Foreign Application Priority Data
Apr. 30, 2015 (CN) .......................... 2015 1 0216716

(51) Int. Cl.
*C07D 249/12* (2006.01)
*C07D 249/08* (2006.01)
(Continued)

(52) U.S. Cl.
CPC .......... *C07D 249/12* (2013.01); *A61K 9/0019* (2013.01); *A61K 9/0056* (2013.01);
(Continued)

(58) Field of Classification Search
CPC ...... A61K 9/0019; A61K 9/0056; A61K 9/48; A61P 19/06; C07D 249/12
See application file for complete search history.

(56) References Cited

U.S. PATENT DOCUMENTS

| | | |
|---|---|---|
| 2013/0345271 A1 | 12/2013 | Zamansky et al. |
| 2014/0005136 A1 | 1/2014 | Quart et al. |
| 2014/0128338 A1* | 5/2014 | Gunic .................. C07D 249/12 514/46 |

FOREIGN PATENT DOCUMENTS

| | | |
|---|---|---|
| CN | 104262277 A | 1/2015 |
| CN | 105820130 A | 8/2016 |

(Continued)

OTHER PUBLICATIONS

Enomoto, Atsushi et al.; "Molecular Identification of a Renal Urate-Anion Exchanger that Regulates Blood Urate Levels"; Letters to Nature, vol. 417; May 23, 2002; pp. 447-452; Supplementary Information A-C.

Fleischmann, Roy et al.; "Pharmacodynamic, pharmacokinetic and tolerability evaluation of concomitant administration of lesinurad and febuxostat in gout patients with hyperuricaemia"; Rheumatology, vol. 53; 2014; pp. 2167-2174.

(Continued)

*Primary Examiner* — Umamaheswari Ramachandran
(74) *Attorney, Agent, or Firm* — Cantor Colburn LLP

(57) ABSTRACT

The present invention relates to the pharmaceutical field for the treatment of hyperuricemia and gout. In particular, the present invention relates to a carboxylic acid urate transporter 1 (URAT1) inhibitor of a general formula (I) containing a diarylmethane structure and a preparation method thereof, and a pharmaceutical composition containing the same and a use thereof in the preparation of medicaments for treating hyperuricemia and gout,

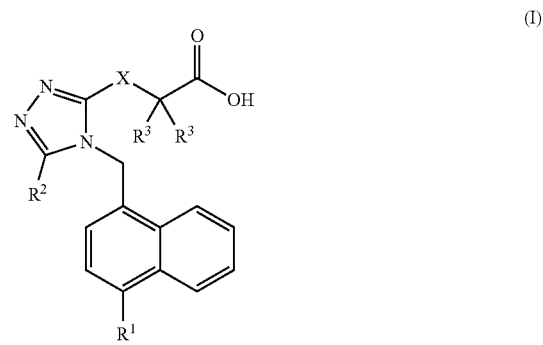

wherein $R^1$ is selected from H, $C_1$-$C_{10}$ alkyl, $C_3$-$C_{10}$ cycloalkyl, F, Cl, Br, I, CN, $NO_2$, $SR^4$ or $OR^4$; $R^2$ is selected from H, F, Cl, Br or I; $R^3$ is selected from H or $C_1$-$C_4$ alkyl; X is selected from S or $CH_2$; wherein $R^4$ is selected from $C_1$-$C_{10}$ alkyl.

10 Claims, No Drawings

(51) Int. Cl.
*A61K 31/4196* (2006.01)
*A61P 19/06* (2006.01)
*A61K 9/00* (2006.01)
*A61K 9/48* (2006.01)

(52) U.S. Cl.
CPC ............ *A61K 9/48* (2013.01); *A61K 31/4196* (2013.01); *A61P 19/06* (2018.01); *C07D 249/08* (2013.01)

(56) References Cited

FOREIGN PATENT DOCUMENTS

| WO | 2009070740 A2 | 6/2009 |
| WO | 2010028190 A2 | 3/2010 |
| WO | 2010135530 A2 | 11/2010 |
| WO | 2014008295 A1 | 1/2014 |

OTHER PUBLICATIONS

Gilchrist, Thomas L. et al.; "Intramolecular Cycloaddition Reactions of in situ Generated Azoalkenes; Synthesis of Pyrrolo[1,2-b]pyridazine Derivatives from α-Haloketone 4-Pentenoylhydrazones"; Synthesis, 1983; pp. 153-154.
International Search Report for International Application No. PCT/CN2016/080468, International Filing Date Apr. 28, 2016, dated Jul. 28, 2017, 5 pages.
STI International, Columbus, Ohio, USA., Oct. 4, 2013 (Oct. 4, 2013).
Written Opinion for International Application No. PCT/CN2016/080468, International Filing Date Apr. 28, 2016, dated Jul. 28, 2017, 6 pages.
Chinese Search Report issued for International Application No. CN201510216716X, International Filing Date Apr. 30, 2015, 2 pages.

* cited by examiner

CARBOXYLIC ACID URAT1 INHIBITOR CONTAINING DIARYLMETHANE STRUCTURE, PREPARATION METHOD AND USE THEREOF

CROSS-REFERENCE TO RELATED APPLICATIONS

This Application is a U.S. National Stage Application of PCT/CN2016/080468 filed on Apr. 28, 2016, which claims the benefit of CN 201510216716.X filed Apr. 30, 2015, each of which is incorporated by reference in its entirety.

TECHNICAL FIELD

The present invention relates to the pharmaceutical field for the treatment of hyperuricemia and gout. In particular, the present invention relates to a carboxylic acid urate transporter 1 (URAT1) inhibitor containing a diarylmethane structure and having therapeutic effect on said diseases, a preparation method thereof, a pharmaceutical composition containing the same, and a use thereof in medicine.

BACKGROUND ART

Gout is a chronic metabolic disease mainly characterized by hyperuricemia and pain caused by deposition of monosodium urate (MSU) at sites such as joints and the like, and is mainly due to purine metabolic disorders and/or uric acid excretion disorders. There are now tens of millions of patients suffering from gout in the world.

The current drugs for the treatment of hyperuricemia and gout mainly include: i) anti-inflammatory analgesic drugs for the control of joint swelling, pain and other symptoms when acute attack of gout occurs, such as colchicine, non-steroidal anti-inflammatory drugs (NSAIDs) and the like; ii) drugs for inhibiting the production of uric acid, such as xanthine oxidase (XO) inhibitors such as allopurinol, oxipurinol, febuxostat and the like; iii) drugs for the excretion of uric acid, such as probenecid, benzbromarone and the like; iv) uricolysis drugs for rapidly lowering blood uric acid when acute attack of gout occurs, such as uricase and pegylated uricase (pegloticase). However, these drugs all have significant side effects, for example, colchicine can cause diarrhea, vomiting, abdominal cramps and other common adverse effects, which is the first indication of its toxicity, with a therapeutically effective dose being close to the dose at which it causes gastrointestinal symptoms; probenecid can cause renal colic and renal dysfunction; benzbromarone has the risk of causing fulminant hepatitis; allopurinol has liver and bone marrow toxicity, allergic reactions and other adverse effects; uricase preparation is administered by injection, which leads to worse patient compliance than that of oral preparation, therefore it is only suitable for lowering blood uric acid when acute attack of gout occurs but not suitable for long-term treatment.

Urate transporter 1 (URAT1) located on the brush-like edge of renal proximal tubular epithelial cell is an important urate transporter in the kidney found in recent years, which is responsible for reabsorption of uric acid in kidney (Enomoto, A.; Kimura, H.; et al. *Nature,* 2002, vol 417, 447-452). Obviously, inhibition of URAT1 would inhibit the reabsorption of uric acid in kidney, increase excretion of uric acid in urine, and thereby achieve the object to lower blood uric acid and control attack of gout. Preclinical study and clinical study from Lesinurad et al. have demonstrated the curative effect of URAT1 inhibitors on the treatment of hyperuricemia and gout (Fleischmann, R.; Kerr, B.; et al. *Rheumatology,* 2014, vol 53, 2167-2174).

Lesinurad (RDEA 594) is an oral drug developed by Ardea Biosciences, Inc. that is capable of inhibiting URAT1 and excreting blood uric acid, and is initially developed from antiviral drug RDEA806 of Valeant Pharmaceuticals International, Inc. (as shown below). A new drug application for Lesinurad has now submitted to EMA (US2013345271 and WO2014008295), the benefits of which have already belonged to Astra Zeneca.

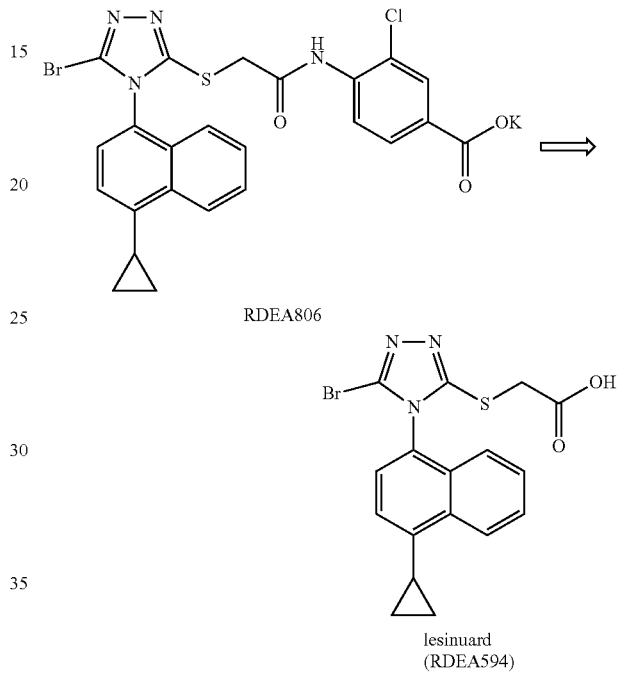

The present invention discloses a carboxylic acid URAT1 inhibitor containing a diarylmethane structure, which can be used in the preparation of medicaments for the treatment of hyperuricemia and gout.

DISCLOSURE OF THE INVENTION

It is an object of the present invention to provide a URAT1 inhibitor having a general formula (I) and a pharmaceutically acceptable salt thereof.

It is another object of the present invention to provide a method for preparing a compound having a general formula (I) and a pharmaceutically acceptable salt thereof.

It is yet another object of the present invention to provide a pharmaceutical composition comprising a compound having a general formula (I) and a pharmaceutically acceptable salt thereof as an active ingredient, and one or more pharmaceutically acceptable carriers, excipients or diluents, and a use thereof in the treatment of gout and hyperuricemia.

The disclosure of the present invention is now described in detail in connection with the objects of the present invention.

The compound of the present invention having the general formula (I) has the following structural formula:

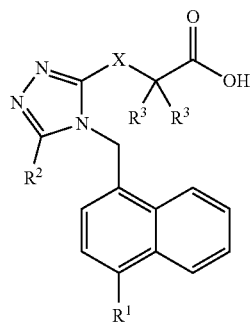

(I)

wherein R[1] is selected from the group consisting of H, $C_1$-$C_{10}$ alkyl, $C_3$-$C_{10}$ cycloalkyl, F, Cl, Br, I, CN, $NO_2$, $SR^4$ and $OR^4$; R[2] is selected from the group consisting of H, F, Cl, Br and I; R[3] is selected from the group consisting of H and $C_1$-$C_4$ alkyl; X is selected from the group consisting of S and $CH_2$; wherein R[4] is selected from $C_1$-$C_{10}$ alkyl.

The following compounds of the general formula (I) are preferred, wherein R[1] is selected from the group consisting of H, $C_1$-$C_4$ alkyl, $C_3$-$C_6$ cycloalkyl, F, Cl, Br, CN, $NO_2$ and $OR^4$; R[2] is selected from the group consisting of H, F, Cl, Br and I; R[3] is selected from the group consisting of H and Me; X is selected from the group consisting of S and $CH_2$; wherein R[4] is selected from $C_1$-$C_4$ alkyl.

More preferred compounds having the general formula (I) are as follows,

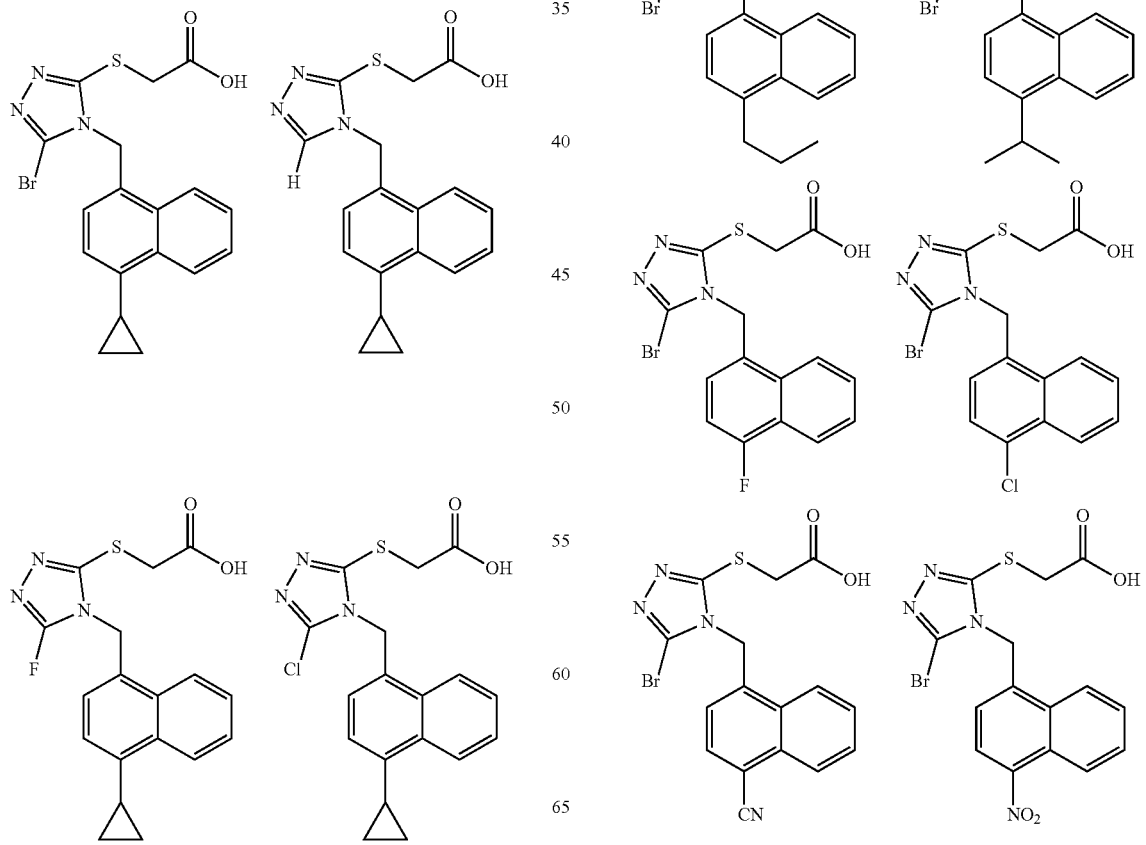

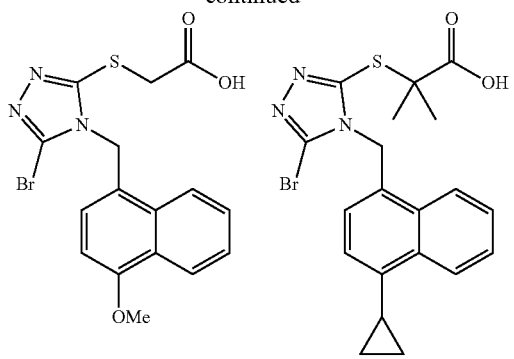
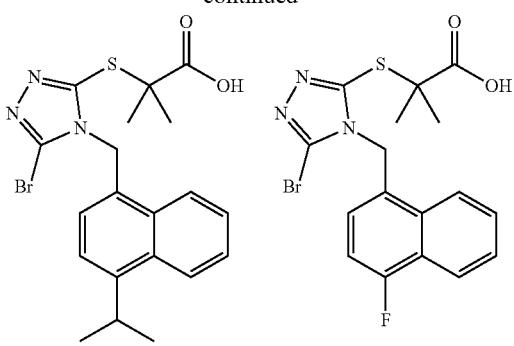
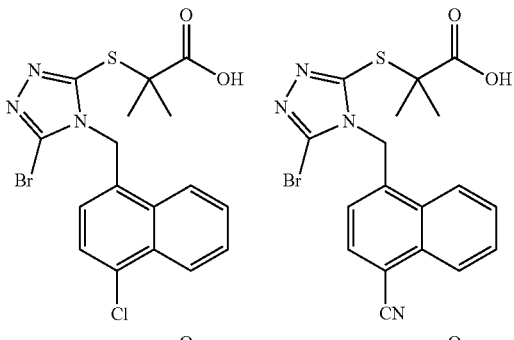
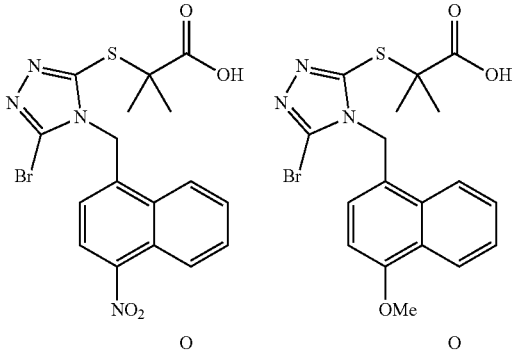
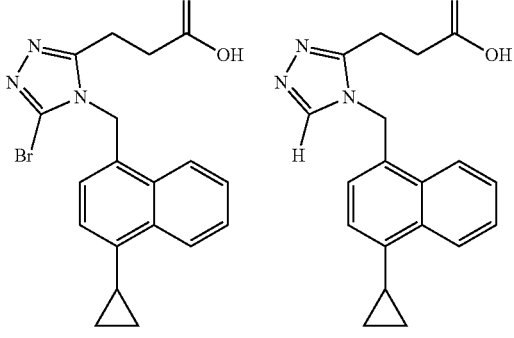
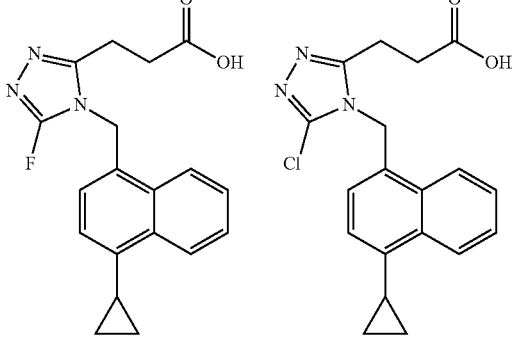

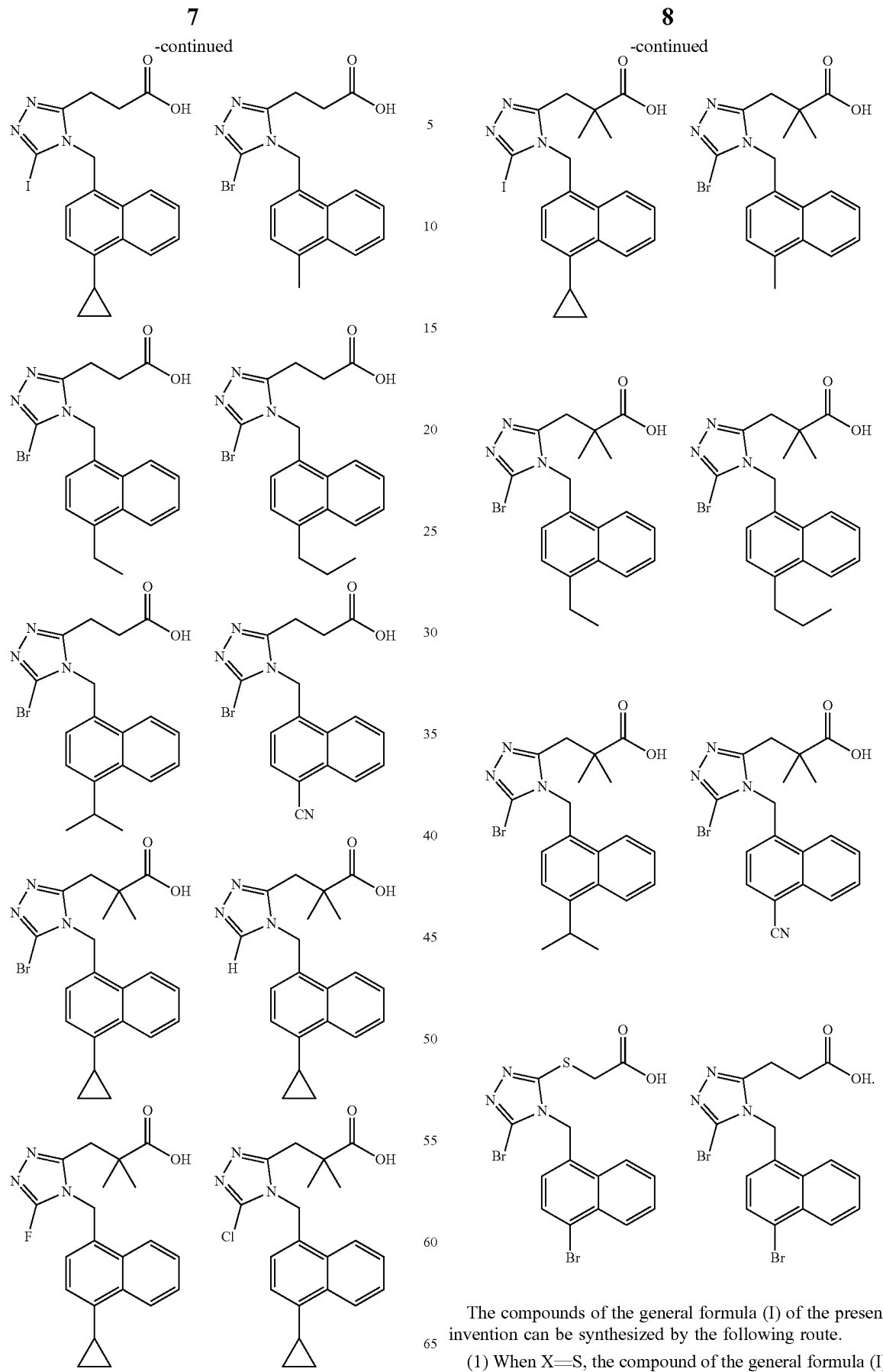
The compounds of the general formula (I) of the present invention can be synthesized by the following route.
(1) When X=S, the compound of the general formula (I) of the present invention is I-A:

I-A can be synthesized by the following route:

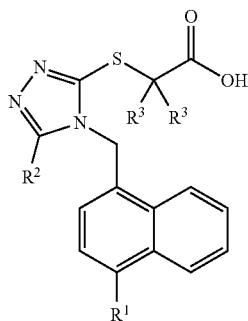
(I-A)

compound IV; compound IV is reacted with thiophosgene in the presence of a base to give a compound V; compound V is first subjected to addition with formylhydrazine to give an intermediate VI which is then treated with a base and cyclized to give a compound VII; compound VII is reacted with an ester of halogenated acid VIII in the presence of a base to give a compound IX, wherein $X^2$ is selected from the group consisting of Cl, Br and I, $R^5$ is selected from $C_1$-$C_{10}$ alkyl; compound IX is treated with a halogenating agent to give compound X, wherein $X^3$ is selected from the group consisting of F, Cl, Br, and 1, and the halogenating agent is selected from the group consisting of $XeF_2$, N-chlorosuccinimide (NCS), N-bromosuccinimide (NBS), N-iodosuccinimide (NIS), dibromohydantoin and dichlorohydantoin; compound X or compound IX is subjected to alkaline

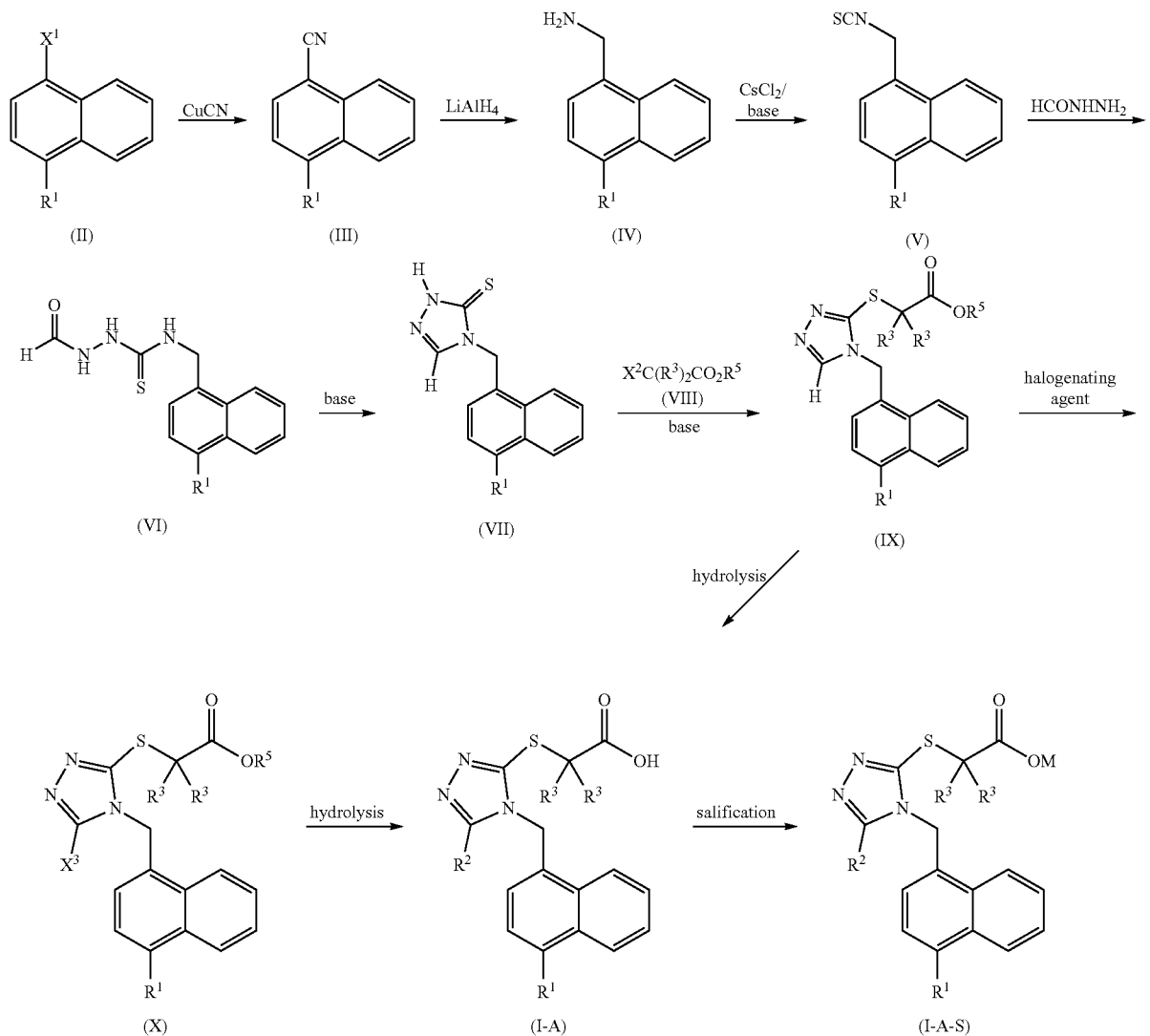

Compound II may be a commercially available chemical raw material or may be prepared by a conventional method in the art.

Compound II is reacted with CuCN to give a compound III, wherein $X^1$ is selected from the group consisting of Cl, Br and I; compound III is reduced with $LiAlH_4$ to give a hydrolysis to give a compound I-A; compound I-A is salified with a base to give its corresponding pharmaceutically acceptable salt I-A-S, wherein M represents a cation in the carboxylate; wherein $R^1$ to $R^3$ are as defined previously.

(2) When $X=CH_2$, the compound of the general formula (I) of the present invention is I-B:

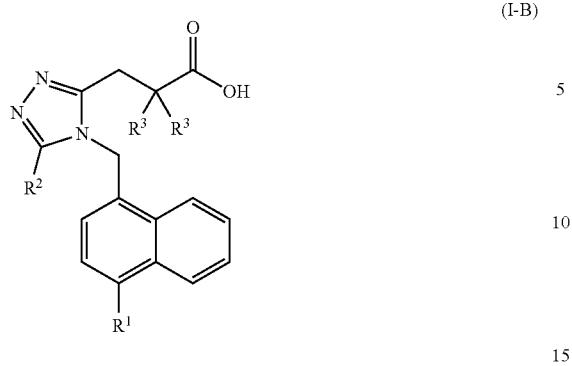
I-B can be synthesized by the following route:
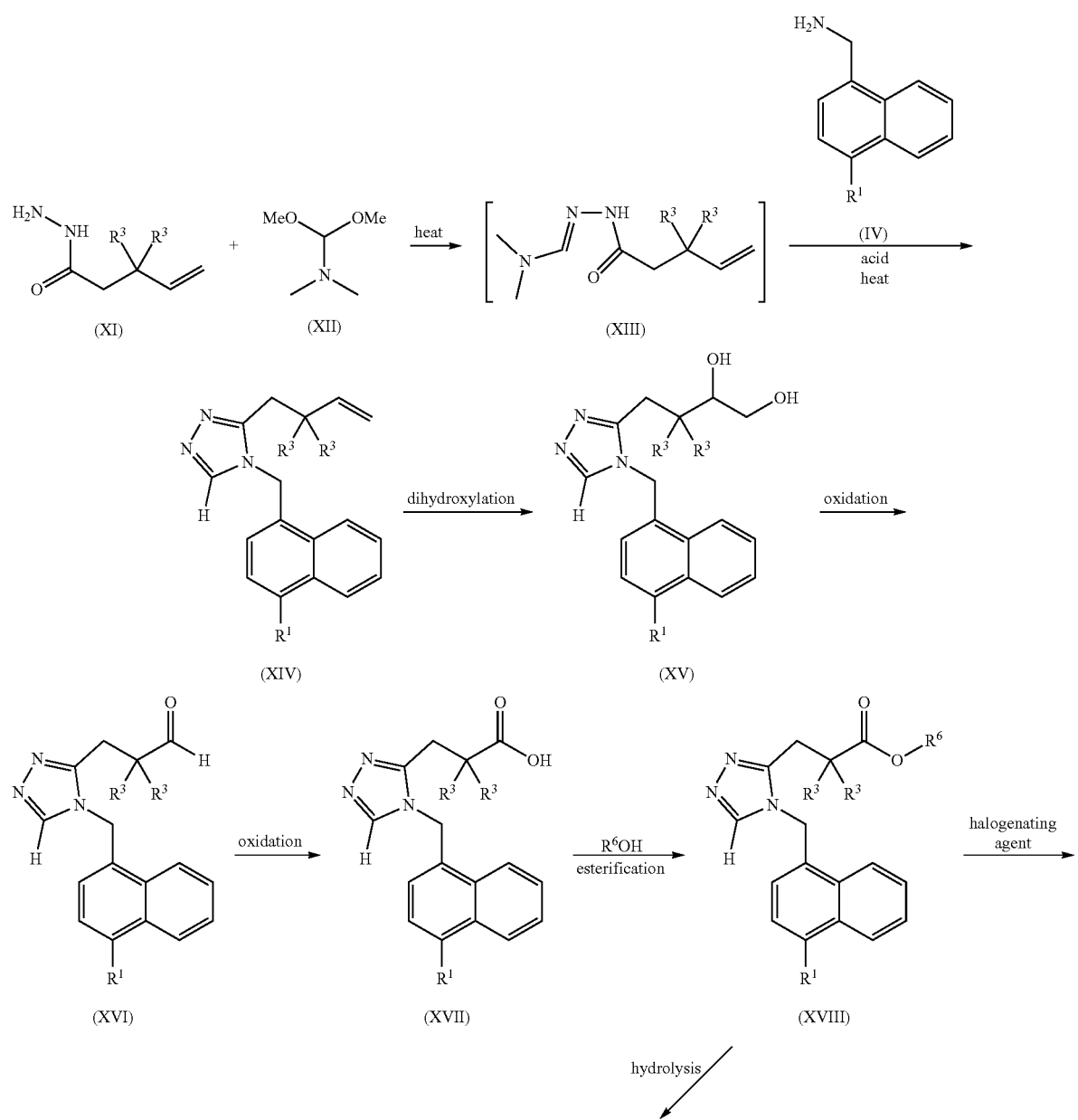

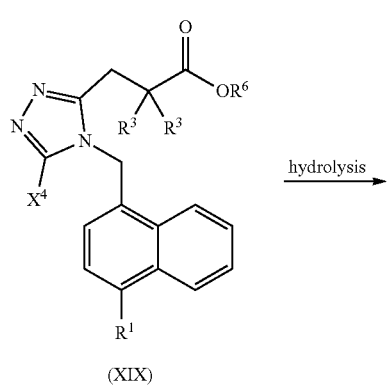 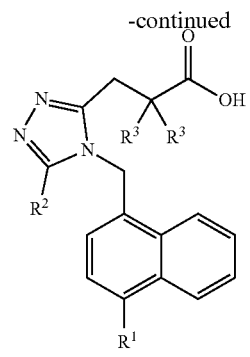 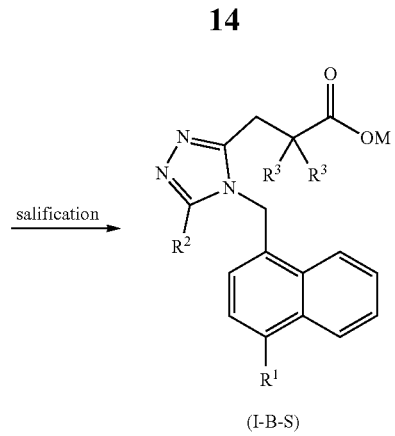

Compound XI may be a commercially available chemical raw material or may be prepared by a conventional method in the art.

Hydrazide XI and N,N-dimethylformamide dimethyl acetal XII are firstly heated to react to give an intermediate XIII, which is not separated but directly reacted with subsequently added naphthylmethylamine IV under acid catalysis, with ring closure being achieved to give a triazole compound XIV; compound XIV is subjected to dihydroxylation to give a vicinal diol compound XV; XV is treated with $NaIO_4$ to give an aldehyde XVI; compound XVI is further oxidized to give a corresponding acid XVII; compound XVII is reacted with an alcohol of $R^6OH$ to give a corresponding ester XVIII, wherein $R^6$ is selected from $C_1$-$C_{10}$ alkyl; compound XVIII is treated with a halogenating agent to give a compound XIX, wherein $X^4$ is selected from the group consisting of F, Cl, Br, and I, and the halogenating agent is selected from the group consisting of $XeF_2$, N-chlorosuccinimide (NCS), N-bromosuccinimide (NBS), N-iodosuccinimide (NIS), dibromohydantoin and dichlorohydantoin; compound XIX or compound XVIII is subjected to alkaline hydrolysis to give a compound I-B; compound I-B is salified with a base to give its corresponding pharmaceutically acceptable salt I-B-S, wherein M represents a cation in the carboxylate; wherein $R^1$ to $R^3$ are as defined previously.

The pharmaceutically acceptable salts of the compound of formula (I) of the present invention include, but are not limited to, pharmaceutically acceptable salts prepared with various inorganic bases such as NaOH, KOH, $Mg(OH)_2$, $Ca(OH)_2$, $Sr(OH)_2$, $Al(OH)_3$, etc., inorganic carbonates such as $Na_2CO_3$, $K_2CO_3$, $MgCO_3$, $CaCO_3$, $SrCO_3$, etc., or organic bases such as amino acids and the like.

The present invention also provides a use of the compounds having a structure of a general formula (I) or a pharmaceutically acceptable salt thereof according to the invention in the preparation of medicaments for the treatment of gout and/or hyperuricemia.

The present invention also provides a pharmaceutical composition comprising a compound having a structure of a general formula (I) or a pharmaceutically acceptable salt thereof according to the present invention, and a suitable carrier or excipient.

The compound of formula (I) according to the present invention may be prepared, in combination with one or more pharmaceutically acceptable carriers, excipients or diluents, into a pharmaceutical composition. The pharmaceutical composition can be prepared into an oral solid preparation, an oral liquid preparation, an injection and the like. The oral solid and liquid preparations include tablets, dispersible tablets, enteric-coated tablets, chewable tablets, orally disintegrating tablets, dragees, granules, dry powders, capsules and solutions. The injections include liquid injections, small-volume injections, large-volume infusion solutions, lyophilized powders for injection and the like.

In the pharmaceutical composition of the present invention, the pharmaceutically acceptable or bromatologically acceptable adjuvant is selected from the group consisting of fillers, binders, disintegrating agents, lubricants, glidants, effervescing agents, flavoring agents, preservatives, coating materials or other excipients.

Wherein the filler comprises a combination of one or more of lactose, sucrose, dextrin, starch, pregelatinized starch, mannitol, sorbitol, calcium monohydrogen phosphate, calcium sulfate, calcium carbonate and microcrystalline cellulose; the binder comprises a combination of one or more of sucrose, starch, povidone, sodium carboxymethylcellulose, hydroxypropylmethylcellulose, hydroxypropylcellulose, methylcellulose, polyethylene glycol, medicinal ethanol and water; the disintegrant comprises a combination of one or more of starch, crospovidone, croscarmellose sodium, low-substituted hydroxypropylcellulose, sodium carboxymethylcellulose and effervescent disintegrant.

The present invention also provides a use of a compound having a structure of a general formula (I) or a pharmaceutically acceptable salt thereof according to the present invention in the preparation of a URAT1 inhibitor.

The present invention also provides a method for treating gout and/or hyperuricemia, comprising administering to a subject in need thereof a compound having a structure of a general formula (I) or a pharmaceutically acceptable salt thereof as defined in the present invention, or a pharmaceutical composition of the present invention.

The compound of general formula (I) of the present invention has a very strong URAT1 inhibiting effect which is generally significantly stronger than that of the URAT1 inhibitors in prior art with a direct covalent linkage between triazole and naphthalene ring as structural features, and can be used as an active ingredient for preparing medicaments for the treatment of gout and hyperuricemia. The activity of the compound of the general formula (I) of the present invention is verified by an experiment of in-vitro inhibition on the absorption of $^{14}C$-labeled uric acid by cells that have already expressed URAT1.

The compound of the general formula (I) of the present invention is effective in a considerable wide range of doses. For example, the daily administration dose is in the range of about 1 mg-1000 mg/person, and administration may be once or several times. The actual administration dosage of the compound of the general formula (I) according to the present invention may be determined by a physician based on the relevant circumstances.

BEST MODE FOR IMPLEMENTATION OF THE INVENTION

The present invention will now be further illustrated in connection with examples. It should be explained that the following examples are only for illustrative purposes but not intended to limit the present invention. Various changes made by a person skilled in the art in light of the teachings of the present invention should be within the scope as claimed in the claims of the present application.

Example 1. Synthesis of Compound I-A-1

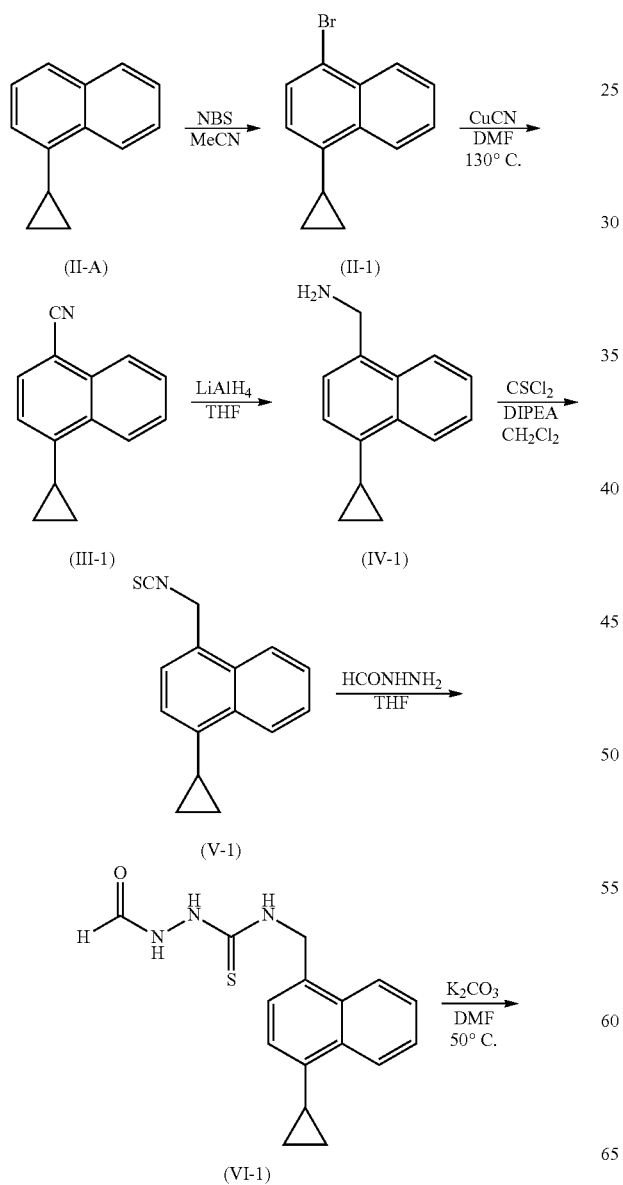

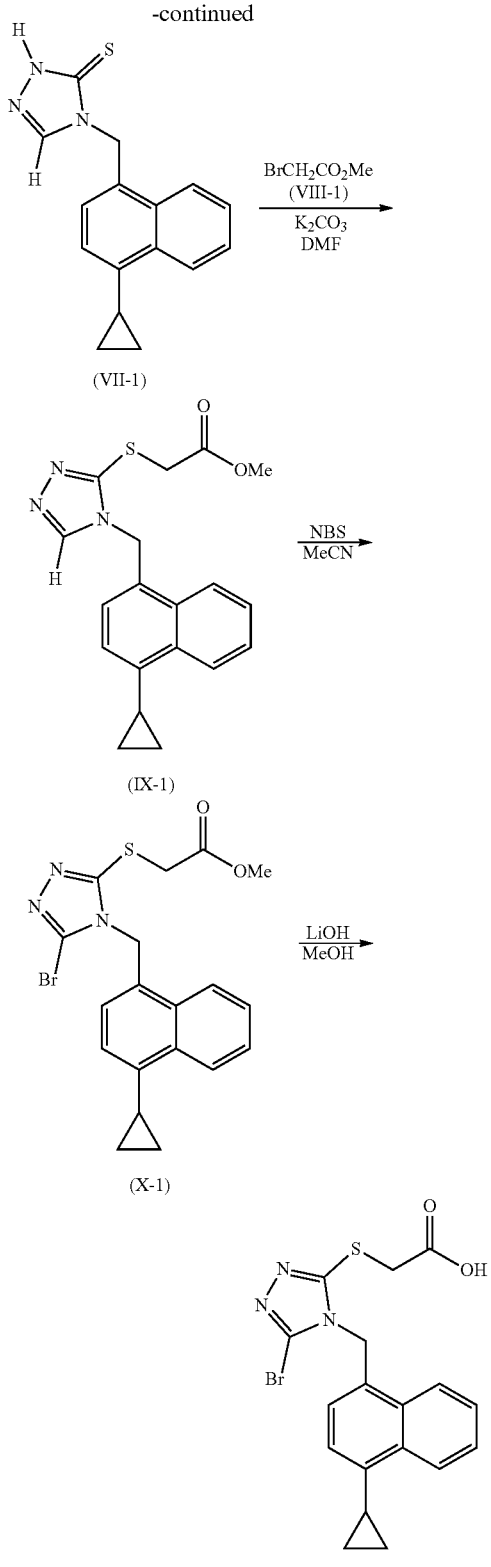

Step 1. Synthesis of Compound II-1

Commercially available compound II-A (8.41 g, 50 mmol) was dissolved in acetonitrile (150 mL) and stirred at room temperature, to which was added NBS (10.68 g, 60 mmol). The resulting reaction mixture was stirred at room temperature overnight, at which point TLC indicated the completion of the reaction.

The reaction mixture was poured into ice water (500 mL), stirred, and extracted with $CH_2Cl_2$ (200 mL×3). The organic phases were combined, washed successively with saturated $Na_2CO_3$ solution (100 mL×3) and 5% saline solution (200 mL), and dried over anhydrous $Na_2SO_4$. The dried organic phase was evaporated on a rotary evaporator to remove the solvent, and the resulting residue was purified by column chromatography to give the product II-1 as a colorless oily substance, yield: 10.01 g, 81%. $^1H$ NMR (DMSO-$d_6$, 400 MHz), δ 8.43-8.47 (m, 1H), 8.13-8.17 (m, 1H), 7.75 (d, 1H, J=7.6 Hz), 7.66-7.72 (m, 2H), 7.15-7.17 (m, 1H), 2.34-2.41 (m, 1H), 1.03-1.08 (m, 2H), 0.69-0.73 (m, 2H).

Step 2. Synthesis of Compound III-1

Compound II-1 (9.89 g, 40 mmol) and CuCN (10.75 g, 120 mmol) were added into DMF (200 mL), and heated with stirring under protection of nitrogen at 130° C. until TLC indicated the completion of the reaction (usually 10 hours).

The reaction mixture was cooled to room temperature, diluted with ethyl acetate (800 mL), and stirred at room temperature for further 5 hours. The resulting mixture was vacuum filtered to remove the solid, and the resulting filtrate was washed with water (500 mL×5) and dried over anhydrous $Na_2SO_4$. The dried organic phase was evaporated on a rotary evaporator to remove the solvent, and the resulting residue was purified by column chromatography to give the product III-1 as a white solid, yield: 6.49 g, 84%. m.p.: 48.5-49.5° C.; $^1H$ NMR (DMSO-$d_6$, 400 MHz), δ 8.51-8.54 (m, 1H), 8.09-8.11 (m, 1H), 8.01 (d, 1H, J=7.2 Hz), 7.73-7.81 (m, 2H), 7.31 (d, 1H, J=7.6 Hz), 2.51-2.56 (m, 1H), 1.11-1.15 (m, 2H), 0.79-0.83 (m, 2H).

Step 3. Synthesis of Compound IV-1

Compound III-1 (6.18 g, 32 mmol) was dissolved in dry THF (100 mL) and stirred, and LiAlH$_4$ (1.90 g, 50 mmol) was slowly added in portions under cooling in an ice-water bath. After completion of the addition, the reaction mixture was stirred at room temperature for further 5 hours, and then heated at reflux under the protection of nitrogen for 1 hour, at which point the reaction was found complete by TLC.

The reaction mixture was carefully and slowly poured into stirred ice water (400 mL), stirred, and extracted with $CH_2Cl_2$ (200 mL×3). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give the product IV-1 as a colorless oil, yield: 5.56 g, 88%. $^1H$ NMR (DMSO-$d_6$, 400 MHz), δ 8.39-8.42 (m, 1H), 8.10-8.13 (m, 1H), 7.52-7.59 (m, 2H), 7.42 (d, 1H, J=7.2 Hz), 7.20 (d, 1H, J=7.2 Hz), 4.14 (s, 2H), 2.31-2.37 (m, 1H), 1.83 (bs, 2H), 1.00-1.05 (m, 2H), 0.65-0.69 (m, 2H).

Step 4. Synthesis of Compound V-1

Compound IV-1 (5.33 g, 27 mmol) and diisopropylethylamine (DIPEA, 11.63 g, 90 mmol) were dissolved in dry $CH_2Cl_2$ (100 mL), and the resulting solution was stirred under cooling in an ice-water bath. Then $CSCl_2$ (3.45 g, 30 mmol) was slowly added dropwise, and after completion of the addition, the resulting solution was stirred at room temperature for further 1 hour, at which point, the reaction was found complete by TLC.

The reaction mixture was carefully and slowly poured into stirred ice water (200 mL) and stirred, the organic phase was separated, and the aqueous phase was extracted with $CH_2Cl_2$ (100 mL×2). The organic phases were combined, washed sequentially with 2% dilute hydrochloric acid (200 mL) and 5% saline solution (200 mL), and dried over anhydrous $Na_2SO_4$. The dried organic phase was evaporated on a rotary evaporator to remove the solvent, and the resulting residue was purified by column chromatography to give the product V-1 as a white solid, yield: 5.36 g, 83%. m.p.: 67.5-69° C.; $^1H$ NMR (DMSO-$d_6$, 400 MHz), δ 8.45-8.49 (m, 1H), 8.05-8.09 (m, 1H), 7.63-7.68 (m, 2H), 7.48 (d, 1H, J=7.2 Hz), 7.25 (d, 1H, J=7.2 Hz), 5.33 (s, 2H), 2.36-2.43 (m, 1H), 1.03-1.07 (m, 2H), 0.70-0.74 (m, 2H).

Step 5. Synthesis of Compound VII-1

Compound V-1 (5.27 g, 22 mmol) was dissolved in THF (50 mL) and stirred at room temperature. Formylhydrazide (1.32 g, 22 mmol) was added, and stirring was continued overnight, at which point, the reaction was found complete by TLC.

The reaction mixture was evaporated on a rotary evaporator to dryness, the resulting residue, i.e., the crude product of VI-1, was dissolved in DMF (60 mL), and solid $K_2CO_3$ (3.04 g, 22 mmol) was added. The reaction mixture was stirred at 50° C. until the reaction was complete (usually 5 hours).

The reaction mixture was cooled to room temperature, poured into ice water (300 mL), stirred, adjusted with hydrochloric acid to pH=5-6, and extracted with $CH_2Cl_2$ (100 mL×5). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give the product VII-1 as a white solid, yield: 4.70 g, 76% (V-1→VII-1). m.p.: 188-189.5° C.; $^1H$ NMR (DMSO-$d_6$, 400 MHz), δ 13.83 (brs, 1H), 8.45-8.48 (m, 1H), 8.28 (s, 1H), 8.14-8.16 (m, 1H), 7.58-7.65 (m, 2H), 7.24 (d, 1H, J=7.2 Hz), 7.19 (d, 1H, J=7.2 Hz), 5.56 (s, 2H), 2.36-2.42 (m, 1H), 1.03-1.08 (m, 2H), 0.69-0.73 (m, 2H).

Step 6. Synthesis of Compound IX-1

Compound VII-1 (4.50 g, 16 mmol) was dissolved in DMF (100 mL) and stirred at room temperature, to which were added solid $K_2CO_3$ (6.63 g, 48 mmol) and methyl bromoacetate VIII-1 (2.75 g, 18 mmol). The resulting reaction mixture was stirred continuously at room temperature until the reaction was found complete by TLC (usually 2 hours).

The reaction mixture was cooled to room temperature, poured into ice water (400 mL), stirred, and extracted with $CH_2Cl_2$ (100 mL×5). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give the product IX-1 as a white solid, yield: 5.26 g, 93%. m.p.: 123-125° C.; $^1H$ NMR (DMSO-$d_6$, 400 MHz), δ 8.62 (s, 1H), 8.46-8.49 (m, 1H), 8.08-8.10 (m, 1H), 7.61-7.67 (m, 2H), 7.22 (d, 1H, J=7.2 Hz), 6.94 (d, 1H, J=7.6 Hz), 5.66 (s, 2H), 4.06 (s, 2H), 3.62 (s, 3H), 2.36-2.43 (m, 1H), 1.03-1.07 (m, 2H), 0.69-0.72 (m, 2H).

Step 7. Synthesis of Compound X-1

Compound IX-1 (3.53 g, 10 mmol) was dissolved in acetonitrile (50 mL) and stirred at room temperature. NBS (2.14 g, 12 mmol) was added, and stirring was continued at room temperature until the reaction was found complete by TLC (usually within 12 hours).

The reaction mixture was poured into ice water (200 mL), stirred, and extracted with $CH_2Cl_2$ (100 mL×3). The organic phases were combined, washed successively with saturated $Na_2CO_3$ solution (100 mL×3) and 5% saline solution (200 mL), and dried over anhydrous $Na_2SO_4$. The dried organic phase was evaporated on a rotary evaporator to remove the solvent, and the resulting residue was purified by column chromatography to give the product X-1 as a colorless oily viscous substance, yield: 3.89 g, 90%. $^1$H NMR (DMSO-$d_6$, 400 MHz), δ 8.48-8.50 (m, 1H), 8.13-8.16 (m, 1H), 7.66-7.71 (m, 2H), 7.18 (d, 1H, J=7.6 Hz), 6.43 (d, 1H, J=7.2 Hz), 5.69 (s, 2H), 4.06 (s, 2H), 3.61 (s, 3H), 2.36-2.41 (m, 1H), 1.02-1.06 (m, 2H), 0.67-0.71 (m, 2H).

Step 8. Synthesis of Compound I-A-1

Compound X-1 (3.46 g, 8 mmol) was added into methanol (50 mL) and stirred at room temperature. A solution consisting of LiOH.$H_2O$ (0.84 g, 20 mmol) and water (3 mL) was added, and stirred at room temperature until the reaction was found complete by TLC (usually 2 hours).

The reaction mixture was poured into ice water (200 mL), stirred, adjusted with hydrochloric acid to pH=2-3, and extracted with $CH_2Cl_2$ (100 mL×4). The organic phases were combined, washed with 5% saline solution (200 mL), and dried over anhydrous $Na_2SO_4$. The dried organic phase was evaporated on a rotary evaporator to remove the solvent, and the resulting residue was purified by column chromatography to give the product I-A-1 as a white solid, yield: 2.78 g, 83%. m.p.: 153.5-154.5° C., $^1$H NMR (DMSO-$d_6$, 400 MHz), δ 13.10 (brs, 1H), 8.48-8.50 (m, 1H), 8.13-8.16 (m, 1H), 7.66-7.71 (m, 2H), 7.18 (d, 1H, J=7.6 Hz), 6.43 (d, 1H, J=7.2 Hz), 5.68 (s, 2H), 3.96 (s, 2H), 2.36-2.40 (m, 1H), 1.02-1.06 (m, 2H), 0.67-0.71 (m, 2H).

Example 2. Synthesis of Compound I-B-1

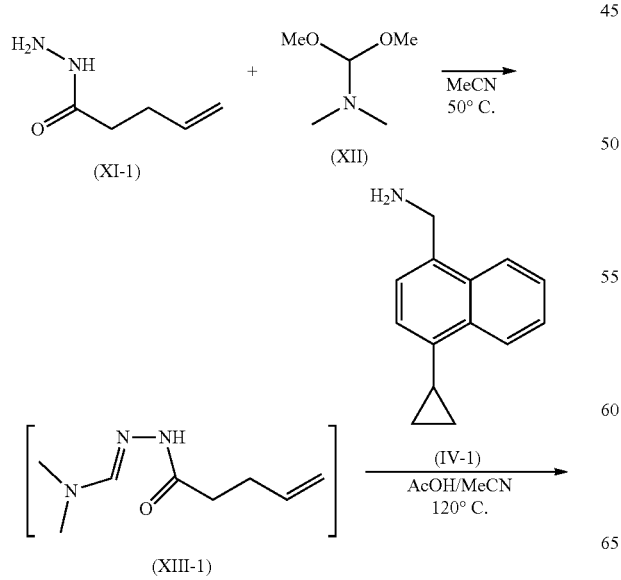

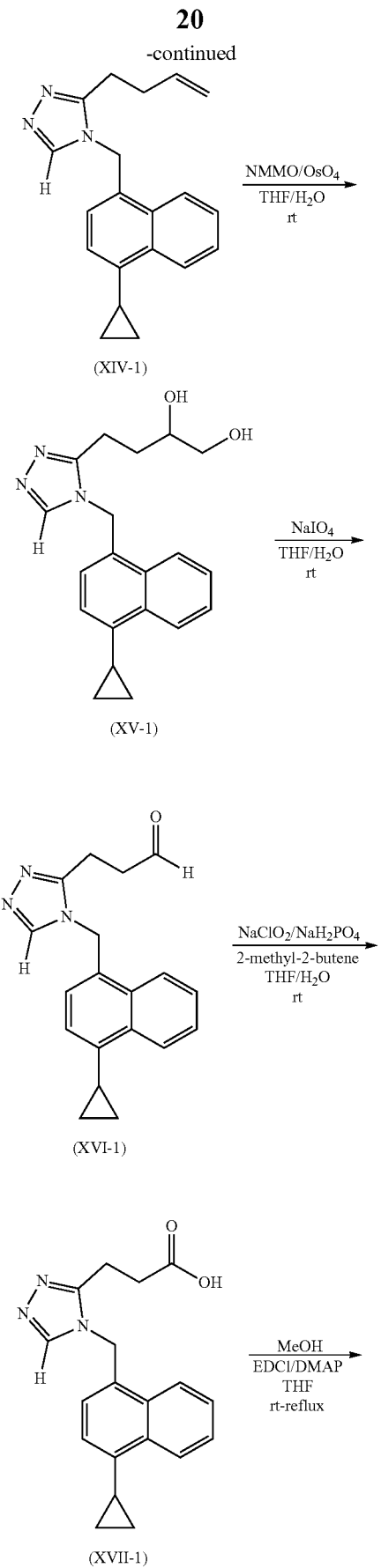

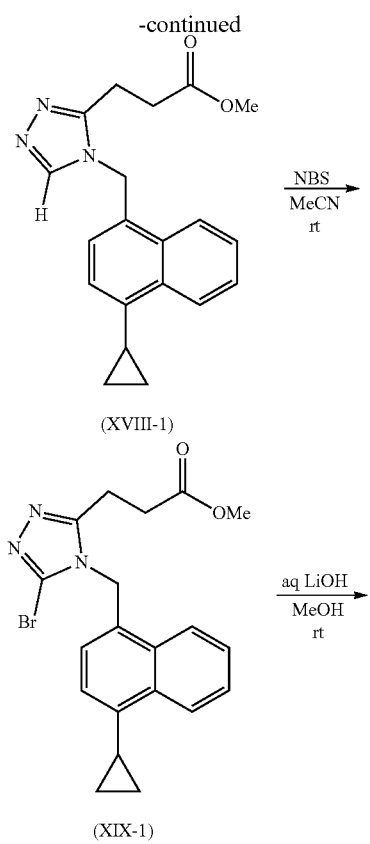

(XVIII-1)

(XIX-1)

(I-B-1)

Step 1. Synthesis of Compound XIV-1

4-Pentenoylhydrazide XI-11 was synthesized according to literature (Gilchrist, T. L.; et al. *Synthesis*, 1983, 153-154). 4-Pentenoylhydrazide XI-1 (11.41 g, 100 mmol) and N,N-dimethylformamide dimethyl acetal XII (11.92 g, 100 mmol) were dissolved in acetonitrile (230 mL), and heated with stirring at 50° C. until the reaction was found complete by TLC (usually about 0.5 to 1 hour).

After completion of the reaction, the reaction mixture was slightly cooled and concentrated on a rotary evaporator to one third of the original volume, at which point a solution of XIII-1 was obtained. 4-cyclopropylnaphthalenemethylamine IV-1 (19.73 g, 100 mmol) and glacial acetic acid (230 mL) were added thereto, and the reaction mixture was stirred under protection of nitrogen at 120° C. overnight, at which point the reaction was found complete by TLC.

The reaction mixture was cooled, poured into ice water (1000 mL), stirred, and extracted with $CH_2Cl_2$ (200 mL×3). The organic phases were combined, washed successively with 1% dilute hydrochloric acid (200 mL), saturated $NaHCO_3$ (200 mL) and 5% saline solution (200 mL), and dried over anhydrous $Na_2SO_4$. The dried organic phase was evaporated on a rotary evaporator to remove the solvent, and the resulting residue was purified by column chromatography to give the product XIV-1, yield: 25.49 g, 84%. MS, m/z=304 ([M+H]$^+$).

Step 2. Synthesis of Compound XV-1

Compound XIV-1 (24.27 g, 80 mmol) was dissolved in a mixed solvent of $THF/H_2O$ (240 mL, 90/10 v/v) and stirred at room temperature, to which were added N-methylmorpholine N-oxide (NMMO, 18.74 g, 160 mmol) and 0.16 M solution of $OsO_4$ in 80% tert-butanol aqueous solution (25 mL, 4 mmol). The reaction mixture was stirred at room temperature overnight and the reaction was found complete by TLC.

The reaction mixture was vacuum filtered, and the filtrate was poured into ice water (600 mL), stirred, and extracted with $CH_2Cl_2$ (200 mL×3). The organic phases were combined, washed successively with $Na_2S_2O_3$ solution (200 mL) and 5% saline solution (200 mL), and dried over anhydrous $Na_2SO_4$. The dried organic phase was evaporated on a rotary evaporator to remove the solvent, and the resulting residue was purified by column chromatography to give the product XV-1, yield: 23.75 g, 88%. MS, m/z=338 ([M+H]$^+$).

Step 3. Synthesis of Compound XVI-1

Compound XV-1 (23.28 g, 69 mmol) was dissolved in a mixed solvent of $THF/H_2O$ (330 mL, 90/10 v/v) and stirred at room temperature, to which was slowly added $NaIO_4$ (44.28 g, 207 mmol) in portions. After completion of the addition, the reaction mixture was stirred continuously at room temperature until the reaction was found complete by TLC.

The reaction mixture was poured into ice water (700 mL), stirred, and extracted with $CH_2Cl_2$ (200 mL×3). The organic phases were combined, washed successively with $Na_2S_2O_3$ solution and 5% saline solution, and dried over anhydrous $Na_2SO_4$. The dried organic phase was evaporated on a rotary evaporator to remove the solvent, and the resulting residue was purified by column chromatography to give the product XVI-1, yield: 16.67 g, 91%. MS, m/z=306 ([M+H]$^+$).

Step 4. Synthesis of Compound XVII-1

Compound XVI-1 (18.32 g, 60 mmol) was dissolved in THF (400 mL) and stirred at room temperature, 2-methyl-2-butene (126.23 g, 1800 mmol) was added, and then a solution prepared by dissolving $NaClO_2$ (16.28 g, 180 mmol) and $NaH_2PO_4$ (43.19 g, 360 mmol) in water (100 mL) was slowly added. After completion of the addition, the reaction mixture was stirred continuously at room temperature until the reaction was found complete by TLC (usually 6 hours).

The reaction mixture was poured into ice water (800 mL), stirred, adjusted with concentrated hydrochloric acid to pH=2-3, and extracted with $CH_2Cl_2$ (200 mL×3). The organic phases were combined, washed with fresh water and dried over anhydrous $Na_2SO_4$. The dried organic phase was evaporated on a rotary evaporator to remove the solvent, and the resulting residue was purified by column chromatography to give the product XVII-1, yield: 16.58 g, 86%. MS, m/z=320 ([M−H]⁻).

Step 5. Synthesis of Compound XVIII-1

Compound XVII-1 (14.46 g, 45 mmol) was dissolved in dry THF (145 mL) and stirred at room temperature. Methanol (14.42 g, 450 mmol) was added, and then N-(3-dimethylaminopropyl)-N'-ethylcarbodiimide hydrochloride (EDCI, 11.50 g, 60 mmol) and 4-dimethylaminopyridine (DMAP, 11.00 g, 90 mmol) were added successively. After completion of the addition, the reaction mixture was stirred at room temperature overnight, and then heated at reflux for 3 hours, at which point the reaction was found complete by TLC.

The reaction mixture was poured into ice water (500 mL), stirred, and extracted with CH₂Cl₂ (200 mL×3). The organic phases were combined, washed successively with 5% dilute hydrochloric acid (300 mL), saturated Na₂CO₃ solution (100 mL) and 5% saline solution (200 mL), and dried over anhydrous Na₂SO₄. The dried organic phase was evaporated on a rotary evaporator to remove the solvent, and the resulting residue was purified by column chromatography to give the product XVIII-1, yield: 12.38 g, 82%. MS, m/z=336 ([M+H]⁺).

Step 6. Synthesis of Compound XIX-1

Compound XVIII-1 (3.35 g, 10 mmol) was dissolved in acetonitrile (50 mL) and stirred at room temperature. NBS (2.14 g, 12 mmol) was added, and stirring was continued at room temperature until the reaction was found complete by TLC (usually within 12 hours).

The reaction mixture was poured into ice water (200 mL), stirred, and extracted with CH₂Cl₂ (100 mL×3). The organic phases were combined, washed successively with saturated Na₂CO₃ solution (100 mL×3) and 5% saline solution (200 mL), and dried over anhydrous Na₂SO₄. The dried organic phase was evaporated on a rotary evaporator to remove the solvent, and the resulting residue was purified by column chromatography to give the product XIX-1, yield: 3.77 g, 91%. MS, m/z=414, 416 ([M+H]⁺).

Step 7. Synthesis of Compound I-B-1

Compound XIX-1 (3.31 g, 8 mmol) was added into methanol (50 mL) and stirred at room temperature. A solution consisting of LiOH.H₂O (0.84 g, 20 mmol) and water (3 mL) was added, and stirred at room temperature until the reaction was found complete by TLC (usually 2 hours).

The reaction mixture was poured into ice water (200 mL), stirred, adjusted with hydrochloric acid to pH=2-3, and extracted with CH₂Cl₂ (100 mL×4). The organic phases were combined, washed with 5% saline solution (200 mL), and dried over anhydrous Na₂SO₄. The dried organic phase was evaporated on a rotary evaporator to remove the solvent, and the resulting residue was purified by column chromatography to give the product I-B-1, yield, 2.59 g, 81%. MS, m/z=398, 400 ([M−H]⁻).

Examples 3-52

The following compounds having the general formula I were synthesized according to the methods of Example 1 and Example 2.

| Example | Structure | Method | ESI-MS |
|---|---|---|---|
| Example 3 | (triazole-S-CH₂-COOH with N-CH₂-naphthalene-cyclopropyl, H substituent) | Example 1 | 338 ([M − H]⁻) |
| Example 4 | (triazole-S-CH₂-COOH with N-CH₂-naphthalene-cyclopropyl, F substituent) | Example 1 | 356 ([M − H]⁻) |
| Example 5 | (triazole-S-CH₂-COOH with N-CH₂-naphthalene-cyclopropyl, Cl substituent) | Example 1 | 372 ([M − H]⁻) |
| Example 6 | (triazole-S-CH₂-COOH with N-CH₂-naphthalene-cyclopropyl, I substituent) | Example 1 | 464 ([M − H]⁻) |

| Example | Structure | Method | ESI-MS |
|---|---|---|---|
| Example 7 | 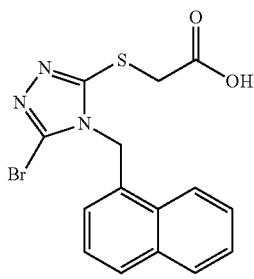 [SMILES: O=C(O)CSc1nnc(Br)n1Cc1cccc2ccccc12] | Example 1 | 376, 378 ([M − H]⁻) |
| Example 8 | 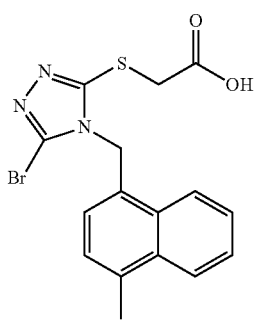 | Example 1 | 390, 392 ([M − H]⁻) |
| Example 9 | 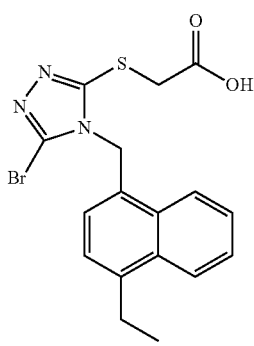 [SMILES: CCc1ccc(Cn2c(Br)nnc2SCC(=O)O)c2ccccc12] | Example 1 | 404, 406 ([M − H]⁻) |
| Example 10 | 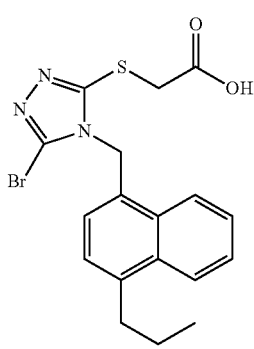 | Example 1 | 418, 420 ([M − H]⁻) |
| Example 11 | 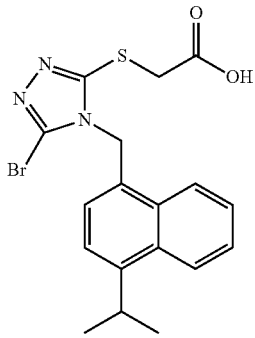 [SMILES: CC(C)c1ccc(Cn2c(Br)nnc2SCC(=O)O)c2ccccc12] | Example 1 | 418, 420 ([M − H]⁻) |
| Example 12 | 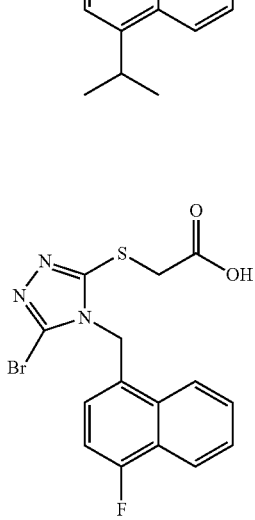 | Example 1 | 394, 396 ([M − H]⁻) |
| Example 13 | 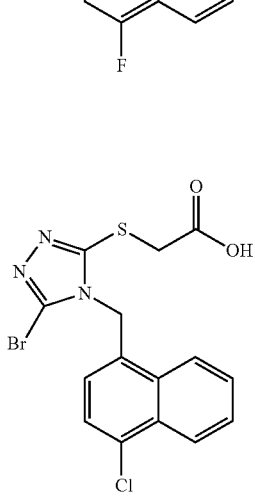 | Example 1 | 410, 412 ([M − H]⁻) |
| Example 14 | 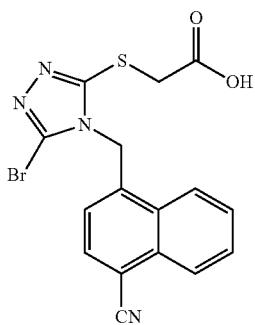 [SMILES: N#Cc1ccc(Cn2c(Br)nnc2SCC(=O)O)c2ccccc12] | Example 1 | 401, 403 ([M − H]⁻) |

-continued
| Example | Structure | Method | ESI-MS |
|---|---|---|---|
| Example 15 | 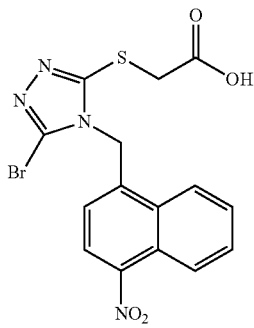 [SMILES: O=C(O)CSc1nnc(Br)n1Cc1ccc([N+](=O)[O-])c2ccccc12] | Example 1 | 421, 423 ([M − H]⁻) |
| Example 16 | 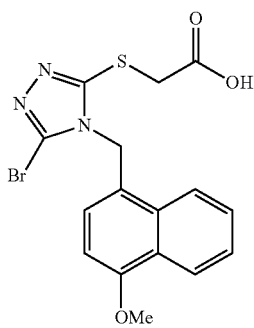 | Example 1 | 406, 408 ([M − H]⁻) |
| Example 17 | 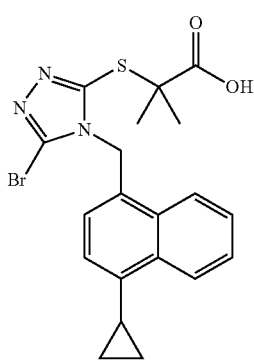 | Example 1 | 444, 446 ([M − H]⁻) |
| Example 18 | 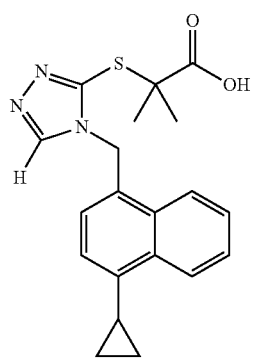 [SMILES: CC(C)(Sc1nncn1Cc1ccc(C2CC2)c2ccccc12)C(=O)O] | Example 1 | 366 ([M − H]⁻) |
-continued
| Example | Structure | Method | ESI-MS |
|---|---|---|---|
| Example 19 | 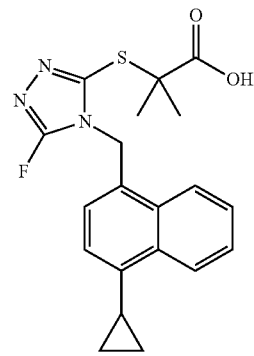 [SMILES: CC(C)(Sc1nnc(I)n1Cc1ccc(C2CC2)c2ccccc12)C(=O)O] | Example 1 | 384 ([M − H]⁻) |
| Example 20 | 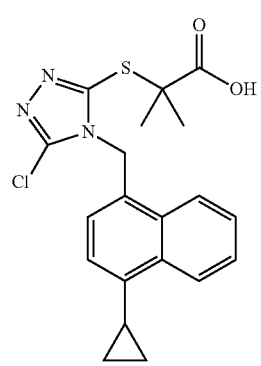 | Example 1 | 409 ([M − H]⁻) |
| Example 21 | 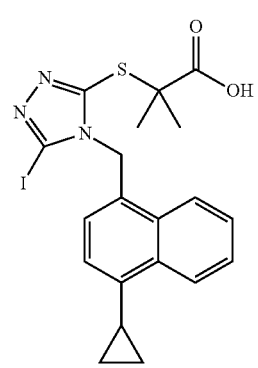 | Example 1 | 492 ([M − H]⁻) |
| Example 22 | 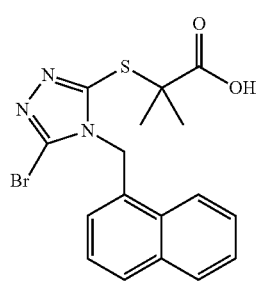 [SMILES: CC(C)(Sc1nnc(Br)n1Cc1cccc2ccccc12)C(=O)O] | Example 1 | 404, 406 ([M − H]⁻) |

-continued
| Example | Structure | Method | ESI-MS |
|---|---|---|---|
| Example 23 | 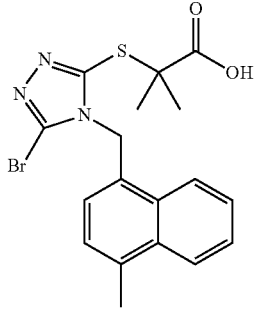 | Example 1 | 418, 420 ([M − H]⁻) |
| Example 24 | 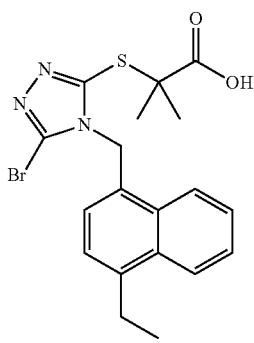 [SMILES: CCc1ccc(Cn2c(Br)nnc2SC(C)(C)C(=O)O)c2ccccc12] | Example 1 | 432, 434 ([M − H]⁻) |
| Example 25 | 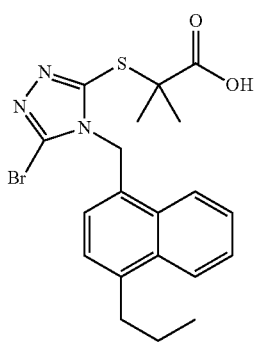 [SMILES: CCCc1ccc(Cn2c(Br)nnc2SC(C)(C)C(=O)O)c2ccccc12] | Example 1 | 446, 448 ([M − H]⁻) |
| Example 26 | 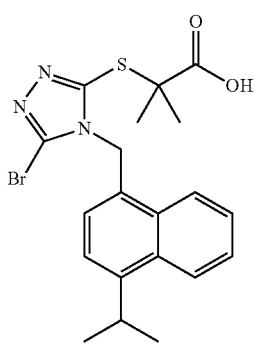 [SMILES: CC(C)c1ccc(Cn2c(Br)nnc2SC(C)(C)C(=O)O)c2ccccc12] | Example 1 | 446, 448 ([M − H]⁻) |
-continued
| Example | Structure | Method | ESI-MS |
|---|---|---|---|
| Example 27 | 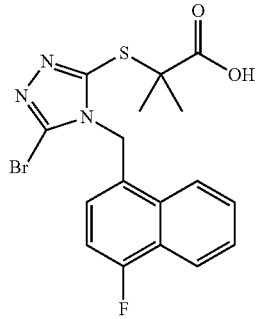 [SMILES: CC(C)(Sc1nnc(Br)n1Cc1ccc(F)c2ccccc12)C(=O)O] | Example 1 | 442, 424 ([M − H]⁻) |
| Example 28 | 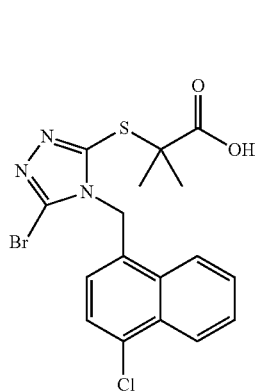 [SMILES: CC(C)(Sc1nnc(Br)n1Cc1ccc(Cl)c2ccccc12)C(=O)O] | Example 1 | 438, 440 ([M − H]⁻) |
| Example 29 | 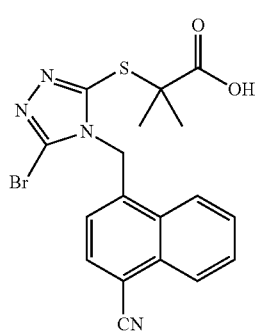 [SMILES: CC(C)(Sc1nnc(Br)n1Cc1ccc(C#N)c2ccccc12)C(=O)O] | Example 1 | 429, 431 ([M − H]⁻) |
| Example 30 | 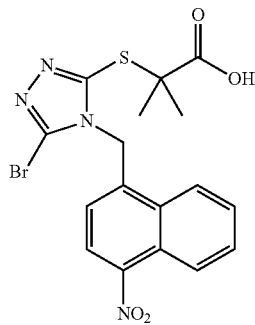 [SMILES: CC(C)(Sc1nnc(Br)n1Cc1ccc([N+](=O)[O-])c2ccccc12)C(=O)O] | Example 1 | 449, 451 ([M − H]⁻) |

-continued
| Example | Structure | Method | ESI-MS |
|---|---|---|---|
| Example 31 | 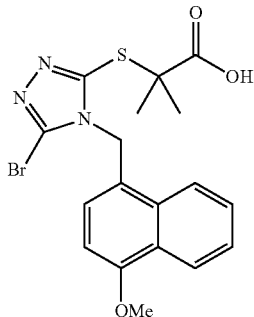 | Example 1 | 434, 436 ([M − H]−) |
| Example 32 | 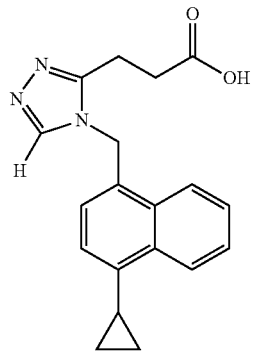 [SMILES: O=C(O)CCc1nncn1Cc1ccc(C2CC2)c2ccccc12] | Example 2 | 320 ([M − H]−) |
| Example 33 | 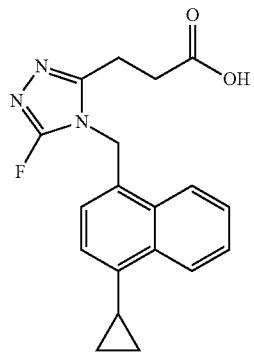 | Example 2 | 338 ([M − H]−) |
| Example 34 | 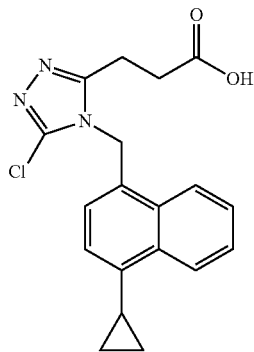 [SMILES: O=C(O)CCc1nnc(Cl)n1Cc1ccc(C2CC2)c2ccccc12] | Example 2 | 354 ([M − H]−) |
-continued
| Example | Structure | Method | ESI-MS |
|---|---|---|---|
| Example 35 | 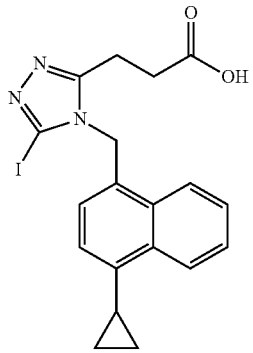 [SMILES: O=C(O)CCc1nnc(I)n1Cc1ccc(C2CC2)c2ccccc12] | Example 2 | 446 ([M − H]−) |
| Example 36 | 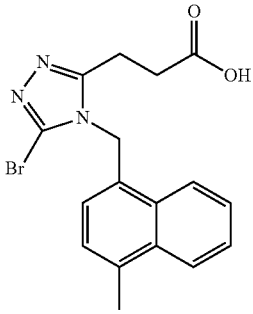 [SMILES: Cc1ccc(Cn2c(Br)nnc2CCC(=O)O)c2ccccc12] | Example 2 | 372, 374 ([M − H]−) |
| Example 37 | 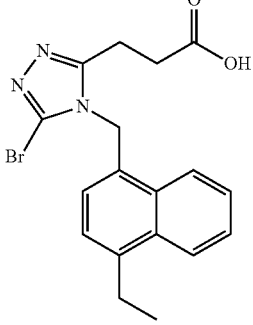 | Example 2 | 386, 388 ([M − H]−) |
| Example 38 | 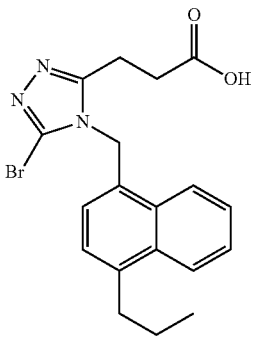 [SMILES: CCCc1ccc(Cn2c(Br)nnc2CCC(=O)O)c2ccccc12] | Example 2 | 400, 402 ([M − H]−) |

-continued
| Example | Structure | Method | ESI-MS |
|---|---|---|---|
| Example 39 | 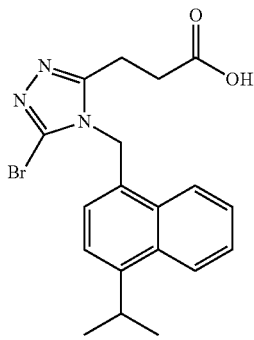 | Example 2 | 400, 402 ([M − H]−) |
| Example 40 | 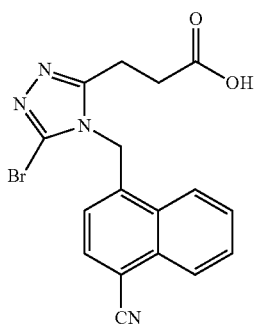 | Example 2 | 383, 385 ([M − H]−) |
| Example 41 | 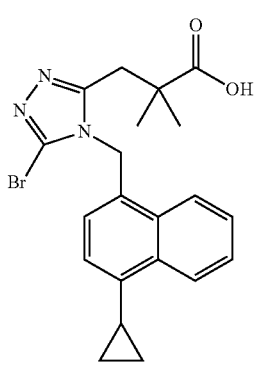 | Example 2 | 426, 428 ([M − H]−) |
| Example 42 | 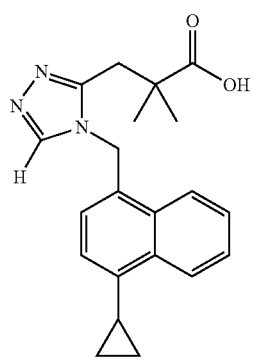 [SMILES: CC(C)(Cc1nncn1Cc1ccc(C2CC2)c2ccccc12)C(=O)O] | Example 2 | 348 ([M − H]−) |
-continued
| Example | Structure | Method | ESI-MS |
|---|---|---|---|
| Example 43 | 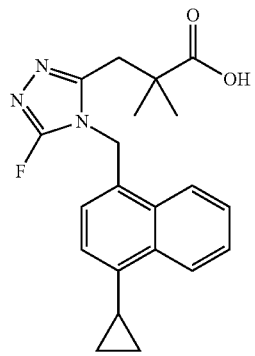 | Example 2 | 366 ([M − H]−) |
| Example 44 | 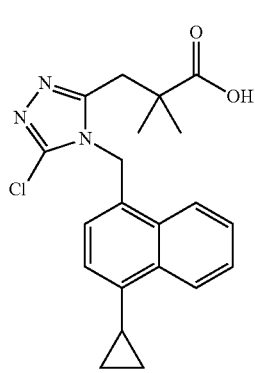 | Example 2 | 382 ([M − H]−) |
| Example 45 | 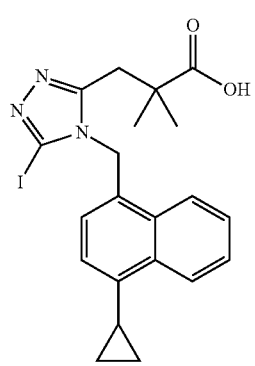 [SMILES: CC(C)(Cc1nnc(I)n1Cc1ccc(C2CC2)c2ccccc12)C(=O)O] | Example 2 | 474 ([M − H]−) |
| Example 46 | 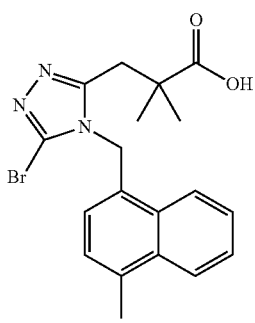 [SMILES: Cc1ccc(Cn2c(Br)nnc2CC(C)(C)C(=O)O)c2ccccc12] | Example 2 | 400, 402 ([M − H]−) |

-continued

| Example | Structure | Method | ESI-MS |
|---|---|---|---|
| Example 47 | 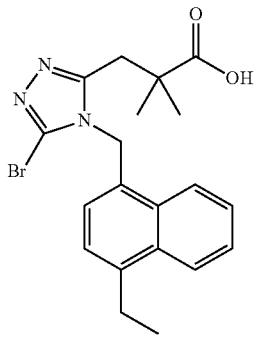 [SMILES: CCc1ccc(Cn2c(Br)nnc2CC(C)(C)C(=O)O)c2ccccc12] | Example 2 | 414, 416 ([M − H]⁻) |
| Example 48 | 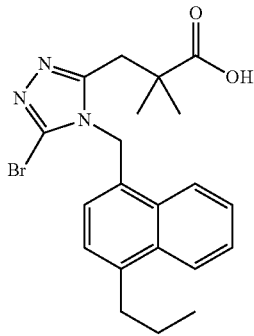 [SMILES: CCCc1ccc(Cn2c(Br)nnc2CC(C)(C)C(=O)O)c2ccccc12] | Example 2 | 428, 430 ([M − H]⁻) |
| Example 49 | 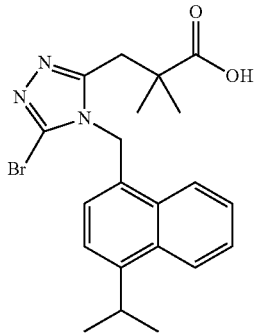 [SMILES: CC(C)c1ccc(Cn2c(Br)nnc2CC(C)(C)C(=O)O)c2ccccc12] | Example 2 | 428, 430 ([M − H]⁻) |
| Example 50 | 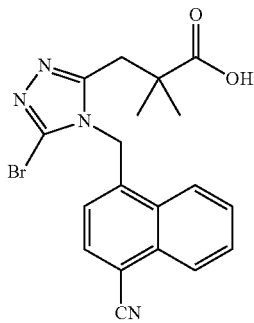 | Example 2 | 411, 413 ([M − H]⁻) |

-continued

| Example | Structure | Method | ESI-MS |
|---|---|---|---|
| Example 51 | 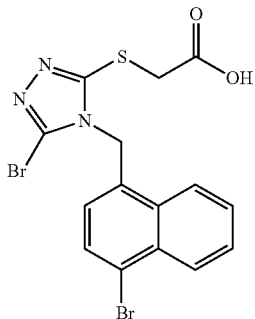 | Example 1 | 455.85 ([M − H]⁻) |
| Example 52 | 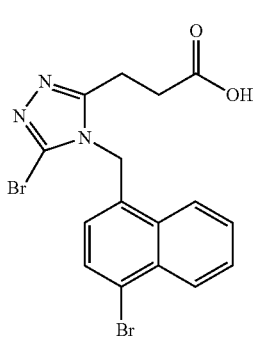 [SMILES: O=C(O)CCc1nnc(Br)n1Cc1ccc(Br)c2ccccc12] | Example 2 | 437.90 ([M − H]⁻) |

Example 53. Synthesis of Sodium Salt I-A-1-S from Compound I-A-1

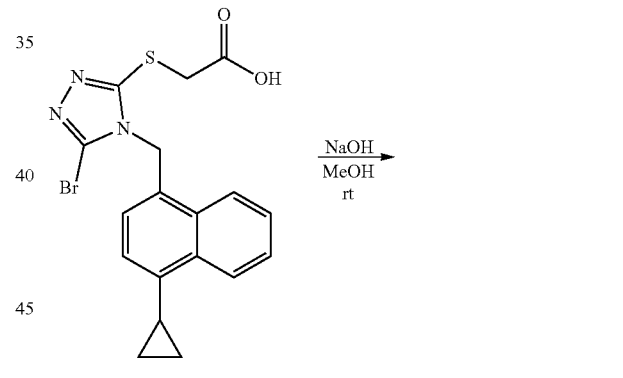

(I-A-1)

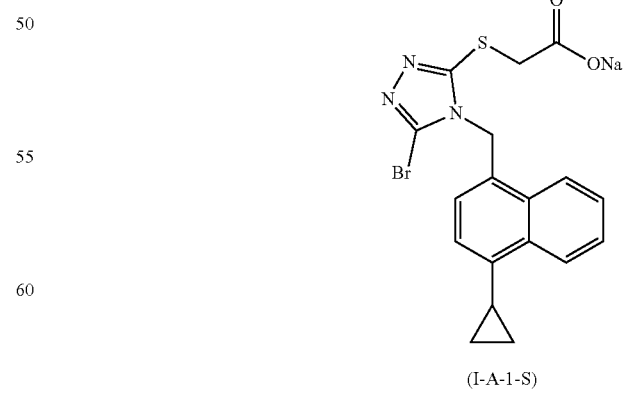

(I-A-1-S)

Compound I-A-1 (0.418 g, 1 mmol) was dissolved in methanol (5 mL) and stirred at room temperature. A solution consisting of NaOH (0.400 g, 1 mmol) and water (1 mL) was slowly added, and after completion of the addition, the reaction mixture was stirred at room temperature for further 10 minutes.

The reaction mixture was evaporated on a rotary evaporator to dryness, the resulting residue was dissolved with methanol (20 mL×2) and reevaporated to dryness so as to remove water in the residue. The resulting residue was further dried on a vacuum oil pump in a 35° C. water bath for 12 hours to give the sodium salt of I-A-1, I-A-1-S, as a white solid, yield: 0.431 g, 98%. $^1$H NMR (DMSO-d$_6$, 400 MHz), δ 8.47-8.50 (m, 1H), 8.15-8.17 (m, 1H), 7.67-7.70 (m, 2H), 7.18 (d, 1H, J=7.2 Hz), 6.35 (d, 1H, J=7.2 Hz), 5.66 (s, 2H), 3.65 (s, 2H), 2.34-2.41 (m, 1H), 1.01-1.05 (m, 2H), 0.68-0.71 (m, 2H).

Examples 54-72. Synthesis of Sodium Salts from Some of the Compounds in Examples 2-52

The compounds having the general formula I listed in the following table can be converted into their corresponding sodium salts I-S according to the method of Example 53.

| Example | Raw material | Product | ESI-MS |
|---|---|---|---|
| Example 54 | Compound of Example 2 | | 398, 400 ([M − Na]⁻) |
| Example 55 | Compound of Example 8 | | 390, 392 ([M − Na]⁻) |
| Example 56 | Compound of Example 9 | | 404, 406 ([M − Na]⁻) |
| Example 57 | Compound of Example 10 | | 418, 420 ([M − Na]⁻) |
| Example 58 | Compound of Example 11 | | 418, 420 ([M − Na]⁻) |
| Example 59 | Compound of Example 17 | | 444, 446 ([M − Na]⁻) |
| Example 60 | Compound of Example 23 | | 418, 420 ([M − Na]⁻) |

-continued

| Example | Raw material | Product | ESI-MS |
|---|---|---|---|
| Example 61 | Compound of Example 24 | [triazole-S-C(CH3)2-C(=O)ONa with N-CH2-(4-ethylnaphthalen-1-yl) and Br] | 432, 434 ([M − Na]−) |
| Example 62 | Compound of Example 25 | [triazole-S-C(CH3)2-C(=O)ONa with N-CH2-(4-propylnaphthalen-1-yl) and Br] | 446, 448 ([M − Na]−) |
| Example 63 | Compound of Example 26 | [triazole-S-C(CH3)2-C(=O)ONa with N-CH2-(4-isopropylnaphthalen-1-yl) and Br] | 446, 448 ([M − Na]−) |
| Example 64 | Compound of Example 36 | [triazole-CH2CH2-C(=O)ONa with N-CH2-(4-methylnaphthalen-1-yl) and Br] | 372, 374 ([M − Na]−) |

-continued

| Example | Raw material | Product | ESI-MS |
|---|---|---|---|
| Example 65 | Compound of Example 37 | [triazole-CH2CH2-C(=O)ONa with N-CH2-(4-ethylnaphthalen-1-yl) and Br] | 386, 388 ([M − Na]−) |
| Example 66 | Compound of Example 38 | [triazole-CH2CH2-C(=O)ONa with N-CH2-(4-propylnaphthalen-1-yl) and Br] | 400, 402 ([M − Na]−) |
| Example 67 | Compound of Example 39 | [triazole-CH2CH2-C(=O)ONa with N-CH2-(4-isopropylnaphthalen-1-yl) and Br] | 400, 402 ([M − Na]−) |
| Example 68 | Compound of Example 41 | [triazole-CH2-C(CH3)2-C(=O)ONa with N-CH2-(4-cyclopropylnaphthalen-1-yl) and Br] | 426, 428 ([M − Na]−) |

-continued

| Example | Raw material | Product | ESI-MS |
|---|---|---|---|
| Example 69 | Compound of Example 46 | (structure) | 400, 402 ([M − Na]−) |
| Example 70 | Compound of Example 47 | (structure) | 414, 416 ([M − Na]−) |
| Example 71 | Compound of Example 48 | (structure) | 428, 430 ([M − Na]−) |
| Example 72 | Compound of Example 49 | (structure) | 428, 430 ([M − Na]−) |

-continued

| Example | Raw material | Product | ESI-MS |
|---|---|---|---|
| Example 73 | Compound of Example 51 | (structure) | 455.86 ([M − Na]−) |
| Example 74 | Compound of Example 52 | (structure) | 437.90 ([M − Na]−) |

Example 75

| Components | Dosage/Granule |
|---|---|
| Sample of Example 1 | 100 mg |
| Microcrystalline cellulose | 30 mg |
| Pregelatinized starch | 20 mg |
| Polyvinylpyrrolidone | 3 mg |
| Magnesium stearate | 2 mg |
| Talc powder | 1 mg |

The active ingredients, pregelatinized starch and microcrystalline cellulose were sieved and mixed thoroughly. Polyvinylpyrrolidone solution was added and mixed. The resulting mixture was prepared into soft material which was sieved and prepared into wet granules. The resulting wet granules were dried at 50-60° C. Magnesium stearate and talc powder were pre-sieved before being added into said granules. Then the said granules were encapsulated.

Example 76

| Components | Dosage/Tablet |
|---|---|
| Sample of Example 2 | 300 mg |
| Microcrystalline cellulose | 80 mg |
| Pregelatinized starch | 70 mg |
| Polyvinylpyrrolidone | 6 mg |
| Sodium carboxymethyl starch | 5 mg |
| Magnesium stearate | 2 mg |
| Talc powder | 2 mg |

The active ingredients, pregelatinized starch and microcrystalline cellulose were sieved and mixed thoroughly.

Polyvinylpyrrolidone solution was added and mixed. The resulting mixture was prepared into soft material which was sieved and prepared into wet granules. The resulting wet granules were dried at 50-60° C. Sodium carboxymethyl starch, magnesium stearate and talc powder were pre-sieved before being added into said granules. Then the said granules were tableted.

Example 77

| Components | Dosage/50 mL |
|---|---|
| Sample of Example 51 | 10 mg |
| Citric acid | 100 mg |
| NaOH | QS (adjusting pH 4.0-5.0) |
| Distilled water | 50 mL |

In distilled water, distilled water and citric acid were firstly added, stirred and dissolved, then the sample was added and slightly heated to dissolve. The pH value was adjusted to be 4.0-5.0 and activated carbon (0.2 g) was added. The resulting solution was stirred at room temperature for 20 minutes and filtered to give the filtrate. The concentration of the filtrate was measured by intermediate control and sub-packaged into ampoule at 5 ml each. The sub-packaged filtrate was high temperature sterilized for 30 minutes to obtain the injection.

Example 78

| Components of granules | Dosage/100 bags |
|---|---|
| Sample of Example 52 | 10.0 g |
| Lactose | 55.0 g |
| Mannitol | 14.0 g |
| Aspartame | 0.05 g |
| Essence | 0.05 g |
| 2% Hydroxypropylmethylcellulose (prepared with pure water) | QS |

Preparation process: the active ingredients and adjuvants were respectively sieved through 100 mesh sieve and mixed thoroughly, and then a formulation amount of the adjuvants were weighed and mixed thoroughly with main ingredients. Then a binding agent was added to prepare soft material, which was granulated with 14 mesh sieve and dried at 55° C. The resulting granules were subjected to size stabilization with 12 mesh sieve, and packaged after the bag weight was weighed.

Example 79

| Components | Use level |
|---|---|
| Sample of Example 53 | 2.0 g |
| Poloxamer | 1.0 g |
| Sodium hydroxide | 0.2 g |
| Citric acid | QS |
| Mannitol | 26.0 g |
| Lactose | 23.0 g |
| Water for injection | 100 mL |

Preparation process: water for injection (80 mL) was taken, the active ingredients, mannitol, lactose and poloxamer were added and stirred to dissolve. 1 mol/L citric acid was added to adjust pH to 7.0-9.0, and water was supplemented to 100 mL. Activated carbon 0.5 g was added and stirred at 30° C. for 20 minutes. The resulting solution was decarbonized, and sterilized by microporous membrane filtration. The filtrate was sub-packaged into ampoule at 1 ml each. The sub-packaged filtrate was pre-freezed for 2 hours and vacuum dried under freezing for 12 hours. After the sample temperature reached room temperature, the sample was dried for further 5 hours to produce a white loose lump, which was sealed.

Example 80. Analysis for In-Vitro Inhibition of Compound on URAT1

(I) Inhibitory Experiment of the Test Compounds at a Concentration of 10 μM on URAT1

After trypsin digestion, the expression cells (HEK293) stably expressing URAT1 gene and mock cells were all inoculated into lysine-coated 24-well culture plates, with the cell inoculation density being $1\times10^5$ cells/well, and cultured in incubator at 37° C., 5% $CO_2$ and saturated humidity for 2 days. The culture fluid in the culture plate was removed, and the cultured cells were washed twice with DPBS and subjected to warm bath in DPBS buffer solution at 37° C. for 10 min, and then a solution (500 μL) containing radioactive labeled probe substrate ([8-$^{14}$C] uric acid) and 10 μM test compound (or blank) was used to substitute for DPBS, with the concentration of [8-$^{14}$C] uric acid being 30 μM and the radiation intensity per well being 0.867 μCi. After 2 min, the reaction was terminated with ice-bathed DPBS buffer solution and washing was carried out for three times. Then 0.1 mol/L NaOH (500 μL) was added into each well to lyse the cells, the lysate was extracted into a scintillation vial and a scintillation fluid (Aquasol-2, 3 mL) was added, and the intensity of radioactivity in the sample was measured using a Tri-Carb 2910TR liquid scintillation analyzer (PerkinElmer, Waltham, USA).

The inhibition rate of the test compound on URAT1 was calculated according to the following formula using the above measured data:

Inhibition rate=(control-test compound)/(control-mock)×100% wherein, control=the intensity of radioactivity corresponding to the well without the test compound test compound=the intensity of radioactivity corresponding to the well with the test compound mock=the intensity of radioactivity corresponding to the well of blank cells untransfected with URAT1

The results were summarized in Table 1 below.

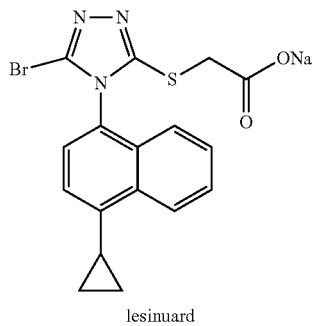

lesinuard

-continued

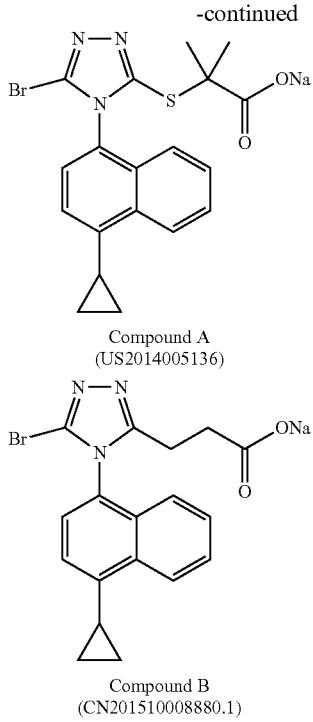

Compound A
(US2014005136)

Compound B
(CN201510008880.1)

TABLE 1

Results of inhibition rate of the compound at a concentration of 10 μM on URAT1

| Test compound | Inhibition rate (%) |
| --- | --- |
| lesinurad | 44 |
| Compound A | 55 |
| Compound B | 50 |
| Compound of Example 1 | 90 |
| Compound of Example 2 | 91 |
| Compound of Example 3 | 60 |
| Compound of Example 4 | 62 |
| Compound of Example 5 | 76 |
| Compound of Example 6 | 78 |
| Compound of Example 7 | 83 |
| Compound of Example 8 | 83 |
| Compound of Example 9 | 84 |
| Compound of Example 10 | 85 |
| Compound of Example 11 | 91 |
| Compound of Example 12 | 76 |
| Compound of Example 13 | 75 |
| Compound of Example 14 | 84 |
| Compound of Example 15 | 70 |
| Compound of Example 16 | 81 |
| Compound of Example 17 | 93 |
| Compound of Example 18 | 78 |
| Compound of Example 19 | 82 |
| Compound of Example 20 | 86 |
| Compound of Example 21 | 82 |
| Compound of Example 22 | 77 |
| Compound of Example 23 | 83 |
| Compound of Example 24 | 84 |
| Compound of Example 25 | 80 |
| Compound of Example 26 | 91 |
| Compound of Example 27 | 83 |
| Compound of Example 28 | 77 |
| Compound of Example 29 | 89 |
| Compound of Example 30 | 81 |
| Compound of Example 31 | 84 |
| Compound of Example 32 | 67 |
| Compound of Example 33 | 68 |
| Compound of Example 34 | 88 |
| Compound of Example 35 | 84 |
| Compound of Example 36 | 82 |
| Compound of Example 37 | 84 |
| Compound of Example 38 | 86 |
| Compound of Example 39 | 92 |
| Compound of Example 40 | 92 |
| Compound of Example 41 | 94 |
| Compound of Example 42 | 71 |
| Compound of Example 43 | 80 |
| Compound of Example 44 | 81 |
| Compound of Example 45 | 82 |
| Compound of Example 46 | 84 |
| Compound of Example 47 | 85 |
| Compound of Example 48 | 85 |
| Compound of Example 49 | 93 |
| Compound of Example 50 | 92 |
| Compound of Example 51 | 95 |
| Compound of Example 52 | 93 |

(II) $IC_{50}$ for Inhibition of the Test Compounds on URAT1

The method of (1) in the present Example was used. The concentration of a certain specific test compound was changed and a series of concentration points (nine concentration points were set between 0.001-10 μM) were set, to obtain the "inhibition rates" of the specific test compound at the above 9 concentration points. $IC_{50}$ values for inhibition of the test compounds on URAT1 were calculated using the PRISM software based on the "inhibition rate" values of the test compound at different concentrations (see Table 2).

TABLE 2

$IC_{50}$ for inhibition of the compounds on URAT1

| Test compound | $IC_{50}$ (μM) |
| --- | --- |
| lesinurad | 7.18 |
| Compound A | 2.13 |
| Compound B | 1.81 |
| Compound of Example 1 | 0.201 |
| Compound of Example 2 | 0.193 |
| Compound of Example 5 | 0.418 |
| Compound of Example 6 | 0.440 |
| Compound of Example 10 | 0.094 |
| Compound of Example 11 | 0.484 |
| Compound of Example 17 | 1.02 |
| Compound of Example 20 | 0.886 |
| Compound of Example 25 | 1.01 |
| Compound of Example 38 | 0.107 |
| Compound of Example 39 | 0.381 |
| Compound of Example 48 | 0.512 |
| Compound of Example 49 | 0.487 |
| Compound of Example 51 | 0.081 |
| Compound of Example 52 | 0.083 |

As can be seen from the results of the above two tables, the compounds of the present invention have very strong inhibitory effect on URAT1, which is generally significantly stronger than that of the URAT1 inhibitor represented by lesinurad, compound A (US 2014005136) and compound B (CN 201510008880.1) with a direct covalent linkage between triazole and naphthalene ring as structural features, and can be used for preparing medicaments for the treatment of gout and hyperuricemia.

The invention claimed is:
1. A compound having a structure of general formula (I) or a pharmaceutically acceptable salt thereof,

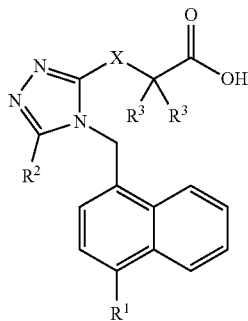
(I)

wherein R[1] is selected from H, $C_1$-$C_{10}$ alkyl, $C_3$-$C_{10}$ cycloalkyl, F, Cl, Br, I, CN, $NO_2$, $SR^4$ or $OR^4$; R[2] is selected from H, F, Cl, Br or I; R[3] is selected from H or $C_1$-$C_4$ alkyl: X is selected from S or $CH_2$; wherein R[4] is selected from $C_1$-$C_{10}$ alkyl; with the proviso that when X is S, then R[1], R[2] and R[3] are not simultaneously H.

2. The compound having the structure of the general formula (I) or the pharmaceutically acceptable salt thereof as defined in claim 1,
wherein R[1] is selected from H, $C_1$-$C_4$ alkyl, $C_3$-$C_6$ cycloalkyl, F, Cl, Br, CN, $NO_2$ or $OR^4$; R[2] is selected from H, F, Cl, Br or I; R[3] is selected from H or Me; X is selected from S or $CH_2$; wherein R[4] is selected from $C_1$-$C_4$ alkyl.

3. The compound of the structure of the general formula (I) or the pharmaceutically acceptable salt thereof as defined in claim 1, which is selected from the following compounds,

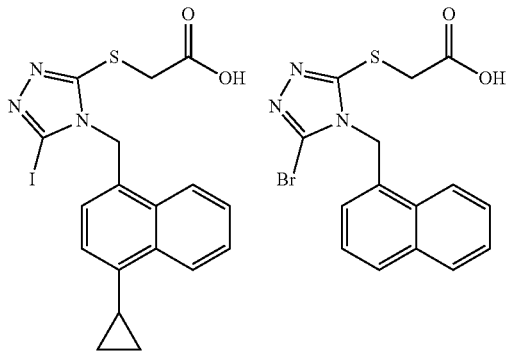

-continued

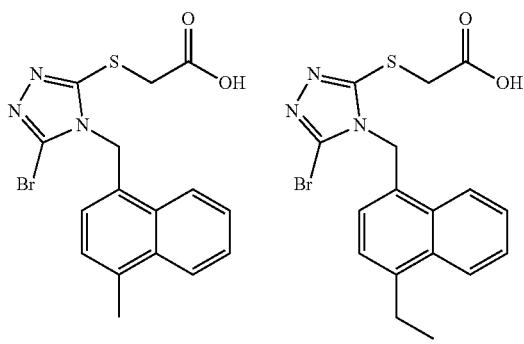

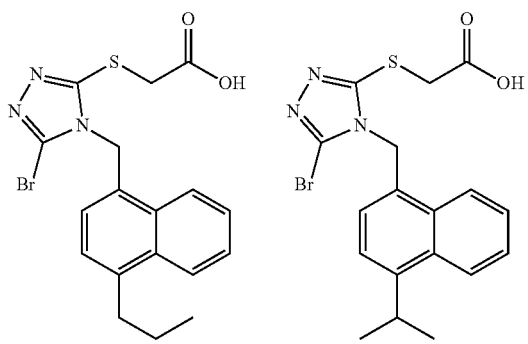

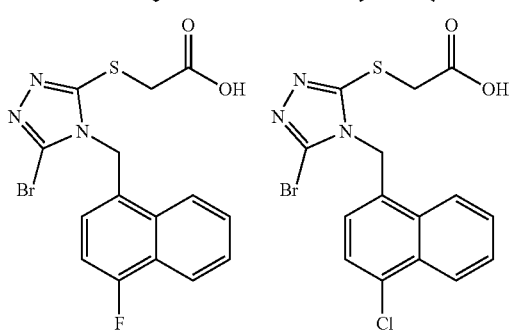

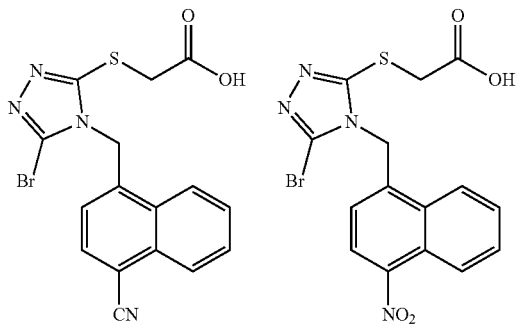

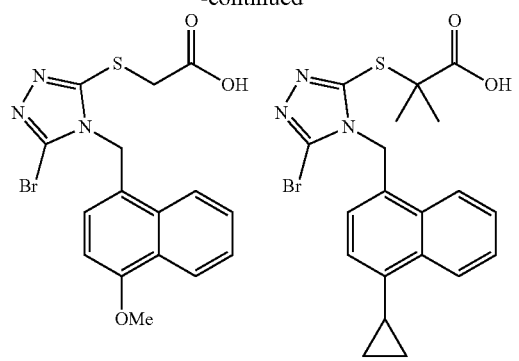
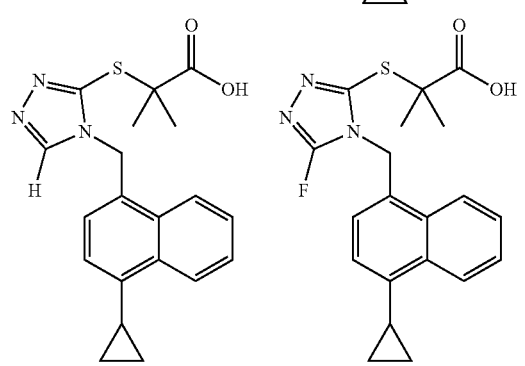
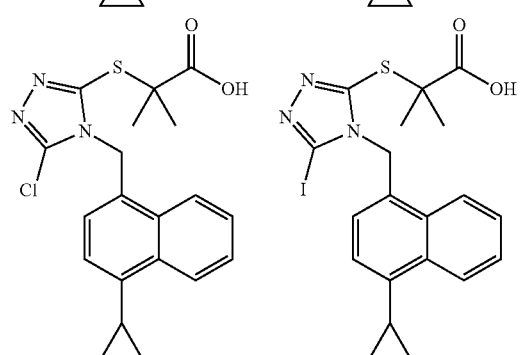
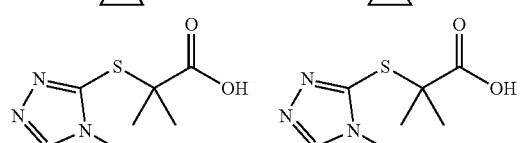
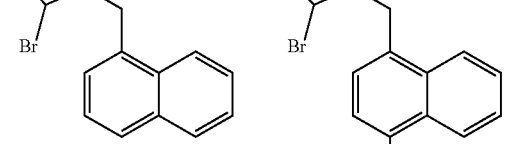
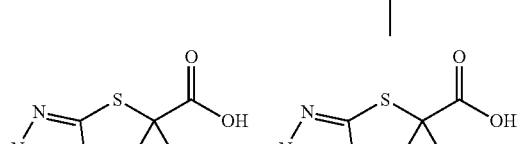
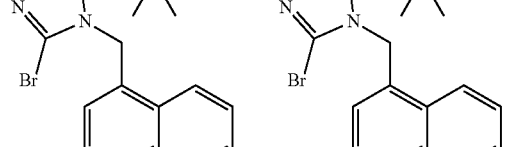
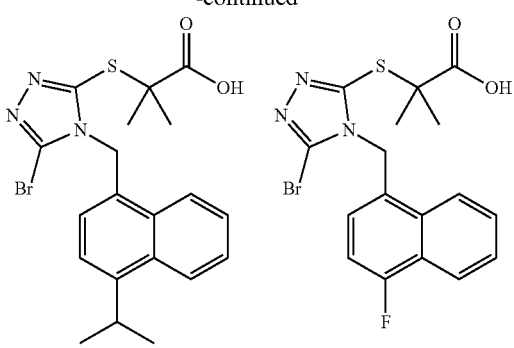
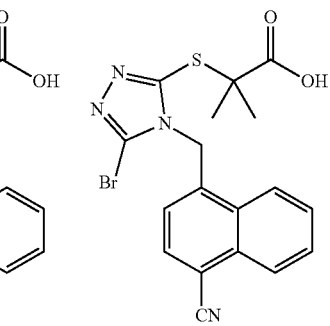
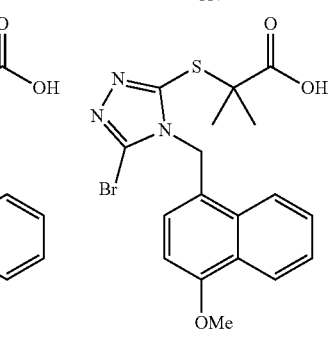
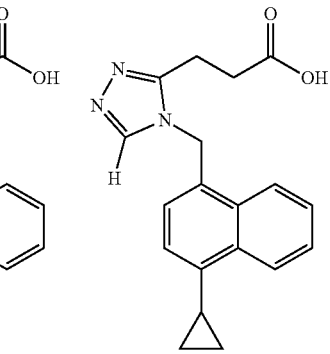
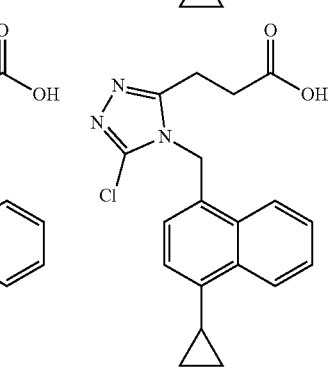

-continued
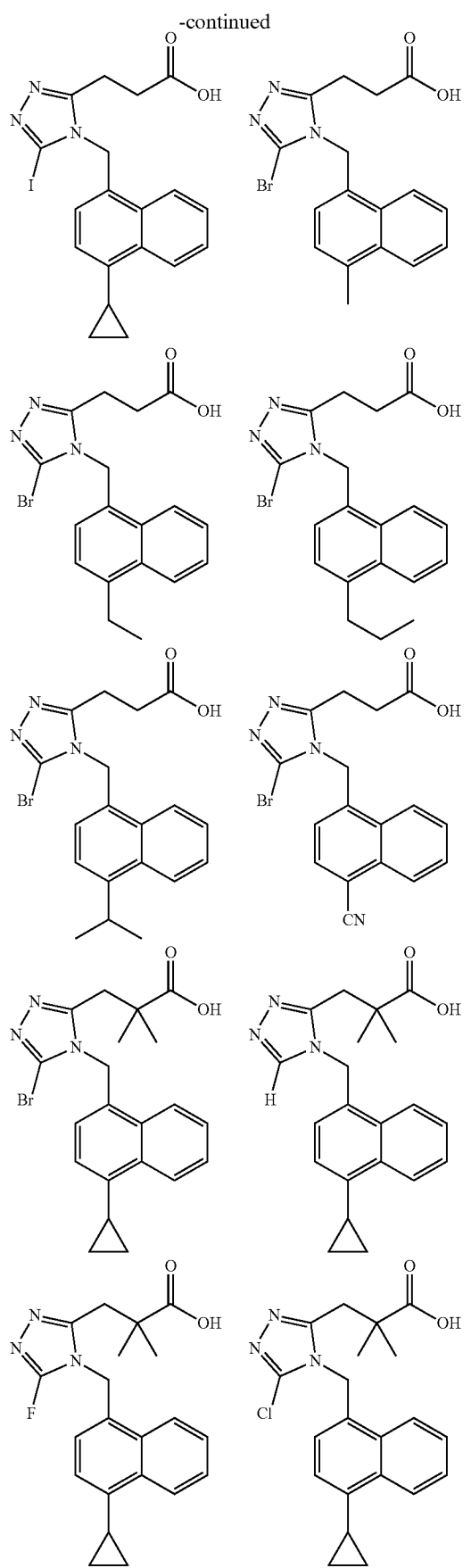
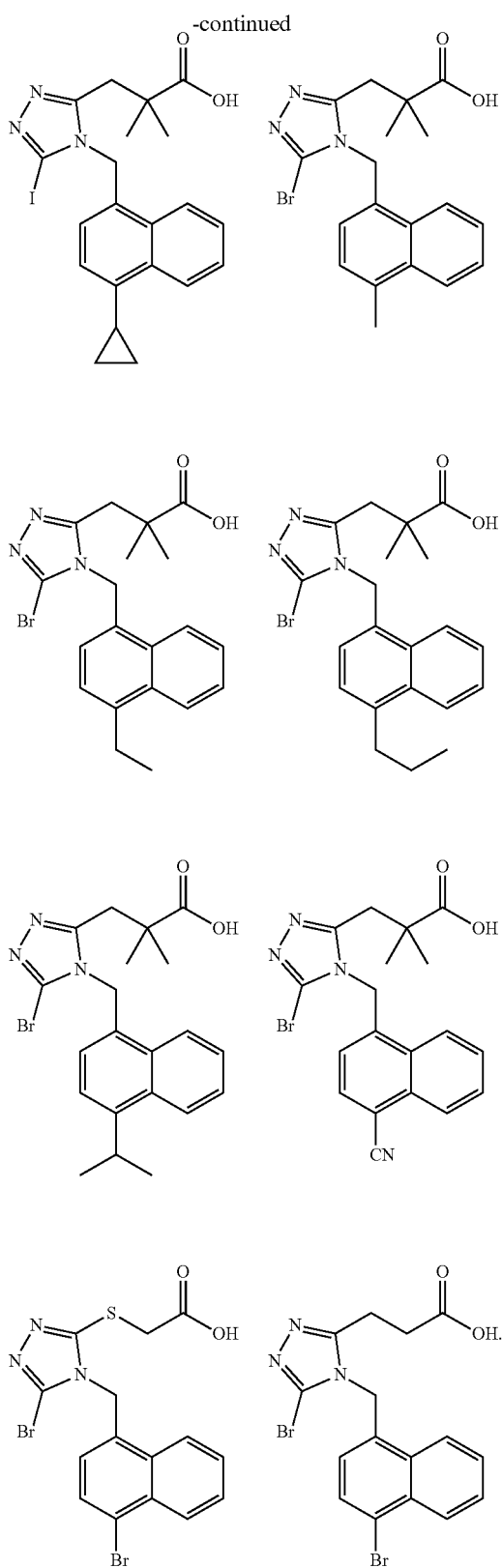
4. A method for preparing a compound having a structure of general formula (I) as defined in claim 1,
wherein when X=S, the compound of the general formula I is I-A, said method comprises the steps of:

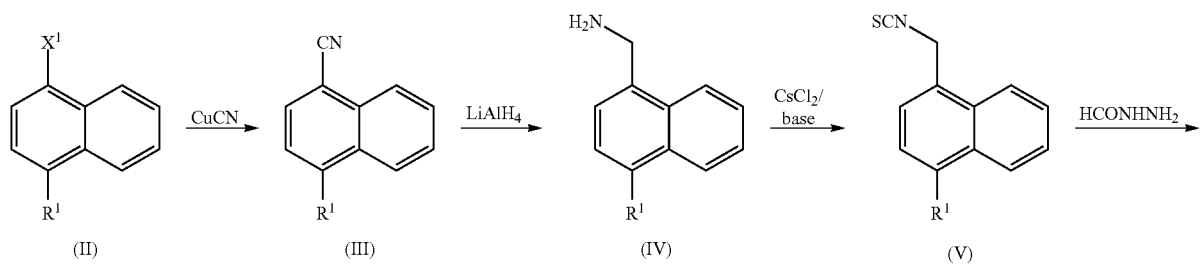

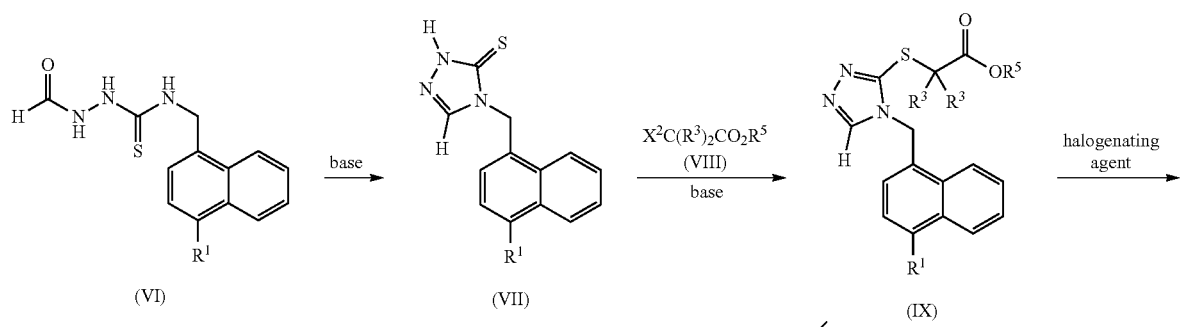

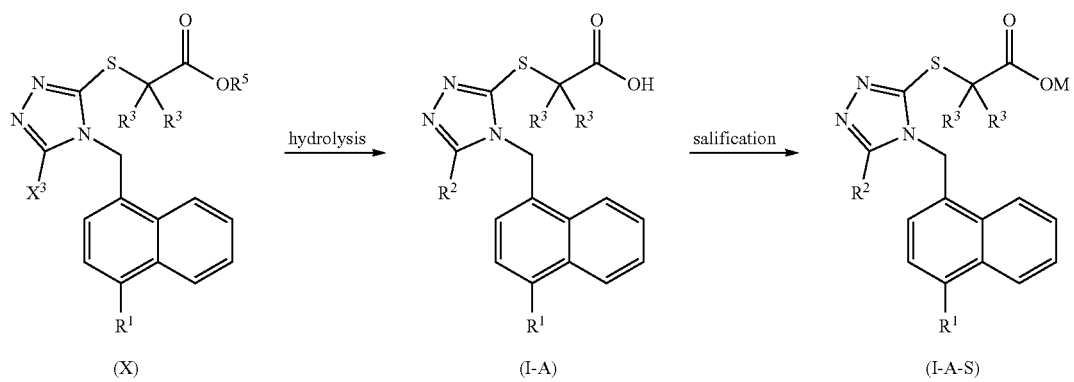

reacting compound II with CuCN to give a compound III, wherein $X^1$ is selected from Cl, Br or I; reducing compound III with LiAlH$_4$ to give a compound IV; reacting compound IV with thiophosgene in the presence of a base to give a compound V; subjecting compound V to addition with formyhydrazine to give an intermediate VI which is then treated with a base and cyclized to give a compound VII; reacting compound VII with an ester of halogenated acid VIII in the presence of a base to give a compound IX, wherein $X^2$ is selected from Cl, Br or I, $R^5$ is selected from $C_1$-$C_{10}$ alkyl; treating compound IX with a halogenating agent to give a compound X, wherein $X^3$ is selected from F, Cl, Br or I, and the halogenating agent is selected from XeF$_2$, N-chlorosuccinimide (NCS), N-bromosuccinimide (NBS), N-iodosuccinimide (NIS), dibromohydantoin or dichlorohydantoin; subjecting compound X or compound IX to alkaline hydrolysis to give a compound I-A; salifying the compound I-A with a base to give its corresponding pharmaceutically acceptable salt I-A-S, wherein M represents a cation in the carboxylate; wherein $R^1$, $R^2$ and $R^3$ are as defined in claim 1; or when X=CH$_2$, the compound of the general formula I is I-B, said method comprises the steps of:

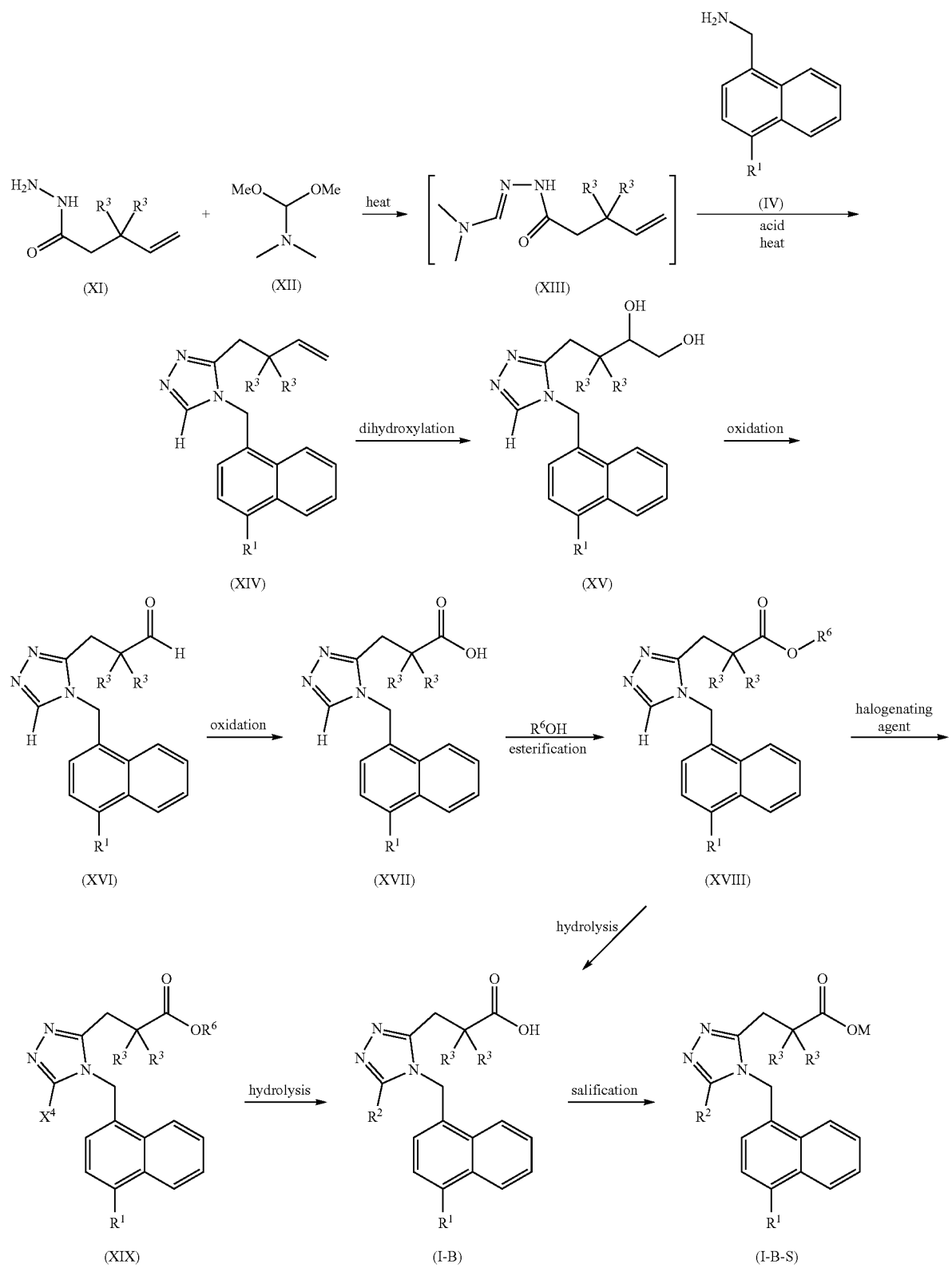

firstly heating hydrazide XI and N,N-dimethylformamide dimethyl acetal XII to react to give an intermediate XIII, which is not separated but directly reacted with subsequently added naphthylmethylamine IV under acid catalysis, with ring closure being achieved to give a triazole compound XIV; subjecting compound XIV to dihydroxylation to give a vicinal diol compound XV; treating XV with NaIO₄ to give an aldehyde XVI;

further oxidizing compound XVI to give a corresponding acid XVII; reacting compound XVII with an alcohol of $R^6OH$ to give a corresponding ester XVIII, wherein $R^6$ is selected from $C_1$-$C_{10}$ alkyl; treating compound XVIII with a halogenating agent to give a compound XIX, wherein $X^4$ is selected from F, Cl, Br or I, and the halogenating agent is selected from $XeF_2$, N-chlorosuccinimide (NCS), N-bromosuccinimide (NBS), N-iodosuccinimide (NIS), dibromohydantoin or dichlorohydantoin; subjecting compound XIX or compound XVIII to alkaline hydrolysis to give a compound I-B; salifying compound I-B with a base to give its corresponding pharmaceutically acceptable salt I-B-S, wherein M represents a cation in the carboxylate; wherein $R^1$, $R^2$ and $R^3$ are as defined in claim 1.

5. A method of preparing a medicament, comprising using a compound having a structure of general formula (I) or a pharmaceutically acceptable salt thereof as defined in claim 1 in the preparation of medicaments for the treatment of gout and/or hyperuricemia.

6. A pharmaceutical composition comprising a compound having a structure of general formula (I) or a pharmaceutically acceptable salt thereof according to claim 1, and a suitable carrier or excipient.

7. The pharmaceutical composition of claim 6, wherein the composition is an oral solid preparation, an oral liquid preparation, or for injection.

8. The pharmaceutical composition of claim 7, wherein the oral solid preparation is in the form of dispersible tablets, enteric-coated tablets, chewable tablets, orally disintegrating tablets, capsules, or granules; the oral liquid preparation is in the form of an oral solution; or the composition for injection is in the form of a liquid injection, a lyophilized powders for injection, a large-volume infusion solution, or a small-volume infusion solution.

9. A method for treating gout and/or hyperuricemia, comprising administering to a subject in need thereof a compound having a structure of general formula (I) or a pharmaceutically acceptable salt as defined in claim 1.

10. A method for treating gout and/or hyperuricemia, comprising administering to a subject in need thereof a compound having a structure of a general formula (I) or a pharmaceutically acceptable salt as a pharmaceutical composition according to claim 6.

* * * * *